(12) United States Patent
Boldt et al.

(10) Patent No.: US 10,278,714 B2
(45) Date of Patent: May 7, 2019

(54) ORTHOPAEDIC SURGICAL INSTRUMENT SYSTEM FOR IMPLANTING A PROSTHETIC PATELLA COMPONENT AND METHOD OF USE

(71) Applicant: DEPUY IRELAND UNLIMITED COMPANY, Cork (IE)

(72) Inventors: Rebecca L. Boldt, Warsaw, IN (US); Matthew S. Wallace, Huntertown, IN (US); Jeremy M. Oden, Huntington, IN (US); Jon M. Edwards, Warsaw, IN (US)

(73) Assignee: DEPUY IRELAND UNLIMTED COMPANY, Ringaskiddy, Co Cork (IE)

( * ) Notice: Subject to any disclaimer, the term of this patent is extended or adjusted under 35 U.S.C. 154(b) by 343 days.

(21) Appl. No.: 15/081,200

(22) Filed: Mar. 25, 2016

(65) Prior Publication Data
US 2016/0278794 A1  Sep. 29, 2016

Related U.S. Application Data

(60) Provisional application No. 62/139,532, filed on Mar. 27, 2015.

(51) Int. Cl.
*A61B 17/17* (2006.01)
*A61F 2/46* (2006.01)
(Continued)

(52) U.S. Cl.
CPC ...... *A61B 17/1767* (2013.01); *A61B 17/8866* (2013.01); *A61F 2/3877* (2013.01);
(Continued)

(58) Field of Classification Search
CPC .................................................. A61B 17/1767
See application file for complete search history.

(56) References Cited

U.S. PATENT DOCUMENTS 2,181,746 A   11/1939 Siebrandt
2,706,475 A * 4/1955 Reynolds, Jr. ..... A61B 17/2812
                                                  602/37
(Continued)

FOREIGN PATENT DOCUMENTS

EP     0992222 A2    4/2000
EP     1967143 A2    9/2008
(Continued)

OTHER PUBLICATIONS

Depuy International, Ltd., PFC Sigma Rotating Platform Knee System With MBT Tray, Surgical Technique Brochure, 2003 (43 Pages), Cat. No. 9068-96-000, Depuy International, Ltd., Leeds, England.

(Continued)

*Primary Examiner* — Zade Coley
(74) *Attorney, Agent, or Firm* — Barnes & Thornburg LLP

(57) ABSTRACT

An orthopedic surgical instrument system includes a compression socket configured for coupling with a selected one of a number of compressible bases. Each compressible base is shaped to conform with a posterior surface of either a dome patella implant component or an anatomical patella implant component.

11 Claims, 19 Drawing Sheets

(51) Int. Cl.
*A61B 17/88* (2006.01)
*A61F 2/38* (2006.01)

(52) U.S. Cl.
CPC .......... *A61F 2/4637* (2013.01); *A61F 2/4684* (2013.01); *A61B 2560/0443* (2013.01); *A61F 2220/0016* (2013.01)

(56) References Cited

U.S. PATENT DOCUMENTS

| | | | |
|---|---|---|---|
| 3,835,849 A | 9/1974 | McGuire | |
| 4,191,861 A | 3/1980 | Walker, Jr. | |
| D260,927 S | 9/1981 | Glenn | |
| D281,622 S | 12/1985 | Diamond | |
| 4,565,192 A | 1/1986 | Shapiro et al. | |
| 4,633,862 A * | 1/1987 | Petersen | A61B 17/158 606/211 |
| 4,692,073 A | 9/1987 | Martindell | |
| 5,002,547 A * | 3/1991 | Poggie | A61B 17/154 606/88 |
| 5,021,055 A | 6/1991 | Burkinshaw et al. | |
| 5,108,401 A | 4/1992 | Insall et al. | |
| 5,116,338 A | 5/1992 | Poggie et al. | |
| 5,129,907 A | 7/1992 | Heldreth et al. | |
| 5,129,908 A * | 7/1992 | Petersen | A61B 17/1677 606/86 R |
| 5,147,365 A | 9/1992 | Whitlock et al. | |
| 5,174,693 A | 12/1992 | Lee et al. | |
| 5,222,955 A | 6/1993 | Mikhail et al. | |
| 5,250,050 A | 10/1993 | Poggie et al. | |
| 5,258,032 A | 11/1993 | Bertin | |
| 5,284,482 A * | 2/1994 | Mikhail | A61B 17/1659 606/86 R |
| 5,284,485 A | 2/1994 | Kammerer et al. | |
| 5,312,409 A | 5/1994 | McLaughlin et al. | |
| 5,382,254 A | 1/1995 | McGarry et al. | |
| 5,415,663 A | 5/1995 | Luckman et al. | |
| 5,470,328 A | 11/1995 | Furnish et al. | |
| 5,484,451 A | 1/1996 | Akopov et al. | |
| D367,531 S | 2/1996 | Price | |
| 5,520,692 A | 5/1996 | Ferrante et al. | |
| 5,536,271 A * | 7/1996 | Daly | A61B 17/1677 606/80 |
| 5,542,947 A | 8/1996 | Treacy | |
| 5,575,793 A | 11/1996 | Carls et al. | |
| 5,582,615 A | 12/1996 | Foshee et al. | |
| 5,593,450 A | 1/1997 | Scott et al. | |
| 5,611,802 A | 3/1997 | Samuelson et al. | |
| 5,626,607 A | 5/1997 | Malecki et al. | |
| 5,667,512 A | 9/1997 | Johnson | |
| 5,716,361 A | 2/1998 | Masini | |
| 5,716,362 A | 2/1998 | Treacy | |
| 5,827,279 A | 10/1998 | Hughett et al. | |
| 5,941,884 A * | 8/1999 | Corvelli | A61B 17/1677 606/102 |
| 5,944,723 A | 8/1999 | Colleran et al. | |
| 5,957,926 A | 9/1999 | Masini | |
| 5,968,051 A * | 10/1999 | Luckman | A61B 17/8802 606/86 R |
| 6,010,509 A | 1/2000 | Delgado et al. | |
| 6,056,754 A | 5/2000 | Haines et al. | |
| 6,080,162 A | 6/2000 | Dye et al. | |
| 6,190,391 B1 * | 2/2001 | Stubbs | A61B 17/88 606/92 |
| 6,205,884 B1 | 3/2001 | Foley et al. | |
| D459,474 S | 6/2002 | Bratt et al. | |
| 6,419,675 B1 | 7/2002 | Gallo, Sr. | |
| D463,550 S | 9/2002 | Sherman | |
| 6,551,316 B1 | 4/2003 | Rinner | |
| 6,589,248 B1 | 7/2003 | Hughes | |
| 6,851,150 B2 | 2/2005 | Chiang | |
| 6,855,150 B2 | 2/2005 | Linehan | |
| 6,866,667 B2 | 3/2005 | Wood et al. | |
| 6,905,514 B2 | 6/2005 | Carignan et al. | |
| D549,331 S | 8/2007 | Tomatsu | |
| 7,344,540 B2 | 3/2008 | Smucker et al. | |
| 7,356,902 B2 | 4/2008 | Snider et al. | |
| 7,566,335 B1 | 7/2009 | Scott et al. | |
| 7,632,279 B2 | 12/2009 | Bastian | |
| 7,780,594 B2 | 8/2010 | Hutton | |
| 7,806,899 B2 | 10/2010 | Hogg et al. | |
| 7,878,989 B2 | 2/2011 | McMinn | |
| 7,891,071 B2 | 2/2011 | Collazo | |
| D634,011 S | 3/2011 | Phillips et al. | |
| D638,541 S | 5/2011 | Claypool | |
| 7,972,383 B2 | 7/2011 | Goldstein et al. | |
| D642,678 S | 8/2011 | Dockstader et al. | |
| D646,389 S | 10/2011 | Claypool et al. | |
| 8,216,242 B2 | 7/2012 | Marchyn et al. | |
| 8,834,574 B2 | 9/2014 | Todd et al. | |
| 8,951,262 B2 | 2/2015 | Kecman et al. | |
| 2002/0115987 A1 | 8/2002 | Hildwein et al. | |
| 2003/0163137 A1 | 8/2003 | Smucker et al. | |
| 2004/0153066 A1 | 8/2004 | Coon et al. | |
| 2004/0162561 A1 | 8/2004 | Marchyn et al. | |
| 2005/0240196 A1 | 10/2005 | Davis et al. | |
| 2006/0058886 A1 | 3/2006 | Wozencroft | |
| 2006/0142777 A1 | 6/2006 | Bastian et al. | |
| 2007/0118141 A1 | 5/2007 | Marchyn et al. | |
| 2007/0150066 A1 | 6/2007 | McMinn | |
| 2007/0162031 A1 | 7/2007 | Hogg et al. | |
| 2007/0179626 A1 | 8/2007 | de la Barrera et al. | |
| 2007/0233142 A1 | 10/2007 | Oliver | |
| 2007/0260227 A1 | 11/2007 | Phan | |
| 2008/0097450 A1 | 4/2008 | Brown et al. | |
| 2008/0114366 A1 | 5/2008 | Smucker et al. | |
| 2008/0177394 A1 * | 7/2008 | Chauhan | A61B 17/1677 623/20.18 |
| 2008/0221569 A1 | 9/2008 | Moore et al. | |
| 2008/0228190 A1 | 9/2008 | Sherry et al. | |
| 2008/0306484 A1 | 12/2008 | Coon et al. | |
| 2009/0088753 A1 | 4/2009 | Aram et al. | |
| 2009/0264737 A1 | 10/2009 | Haechler et al. | |
| 2009/0326661 A1 | 12/2009 | Wright et al. | |
| 2010/0030223 A1 | 2/2010 | Keller | |
| 2010/0114154 A1 * | 5/2010 | Snell | A61B 17/8866 606/205 |
| 2010/0121389 A1 | 5/2010 | Librot | |
| 2010/0152742 A1 | 6/2010 | Nevelös et al. | |
| 2010/0160924 A1 | 6/2010 | Soliman | |
| 2010/0168753 A1 | 7/2010 | Edwards et al. | |
| 2010/0204701 A1 | 8/2010 | Tallarida et al. | |
| 2011/0066193 A1 * | 3/2011 | Lang | A61B 5/4528 606/86 R |
| 2012/0078261 A1 | 3/2012 | Kecman et al. | |
| 2013/0023883 A1 | 1/2013 | Wright et al. | |
| 2013/0023890 A1 * | 1/2013 | Kecman | A61B 17/1767 606/96 |
| 2013/0030443 A1 * | 1/2013 | Wright | A61B 17/1767 606/96 |
| 2013/0030539 A1 | 1/2013 | Wright et al. | |
| 2013/0035693 A1 | 2/2013 | Wright et al. | |
| 2013/0079787 A1 | 3/2013 | Spencer Jones et al. | |
| 2013/0079788 A1 | 3/2013 | Spencer Jones et al. | |
| 2013/0079789 A1 | 3/2013 | Randle et al. | |
| 2013/0211410 A1 | 8/2013 | Landes et al. | |
| 2014/0094813 A1 * | 4/2014 | Clever | A61B 17/1767 606/88 |
| 2014/0094818 A1 * | 4/2014 | Wallace | A61B 17/8866 606/96 |
| 2014/0094819 A1 * | 4/2014 | Clever | A61B 17/1767 606/96 |
| 2014/0094820 A1 * | 4/2014 | Clever | A61B 17/1767 606/96 |

FOREIGN PATENT DOCUMENTS

| | | |
|---|---|---|
| FR | 2737848 A1 | 2/1997 |
| WO | 9945856 A1 | 9/1999 |
| WO | 2005110249 A1 | 11/2005 |

(56) References Cited

FOREIGN PATENT DOCUMENTS

| WO | 2008112996 A1 | 9/2008 |
|----|---------------|--------|
| WO | 2013003730 A1 | 1/2013 |

OTHER PUBLICATIONS

Depuy Orthopaedics, Inc., LCS High Performance Instruments, Surgical Technique Guide, 2008, (44 Pages), Pub. No. 0612-85-506, Depuy Orthopaedics, Inc., Warsaw, IN.
Depuy Orthopaedics, Inc. Sigma High Performance Instruments, Classic Surgical Technique, 2010, (52 Pages), Pub. No. 0612-89-510, Depuy Orthopaedics, Inc., Warsaw, IN.
Depuy Orthopaedics, Inc., Sigma High Performance Instruments, Design Rationale, 2007 (12 Pages), Pub. No. 0612-54-506 (Rev. 2), Depuy Orthopaedics, Inc., Warsaw, IN.
European Search Report, European Pat. App. No. 11175824.9-2310, dated Dec. 16, 2011 (7 Pages).
European Search Report, European Pat. App. No. 12191753.8-2310, dated Jan. 3, 2013 (6 Pages).
European Search Report for European Application No. 12174683.8-2310, dated Sep. 3, 2012, 6 pages.
European Search Report for European Application No. 12174682.0-2310, dated Sep. 5, 2012, 6 pages.
International Search Report, International Application No. PCT/US12/44947, dated Oct. 12, 2012, 3 pages.
European Search Report for European Application No. 12186675.0-2310, dated Dec. 12, 2012, 7 pages.
European Search Report for European Application No. 12186700.6-2310, Dec. 13, 2012, 8 pages.
European Search Report for European Application No. 12186728.7-2310, dated Dec. 14, 2012, 8 pages.
European Search Report for European Application No. 13186401.9-1654, dated Jan. 17, 2014, 7 pages.
European Search Report for European Application No. 13186416.7-1654, dated Dec. 6, 2013, 7 pages.
Extended European Search Report, European Application No. 16160477.2-1654, dated May 11, 2016, 8 pages.

* cited by examiner

ORTHOPAEDIC SURGICAL INSTRUMENT SYSTEM FOR IMPLANTING A PROSTHETIC PATELLA COMPONENT AND METHOD OF USE

This application claims priority under 35 U.S.C. § 119 to U.S. Provisional Patent App. No. 62/139,532, which was filed on Mar. 27, 2015 and is expressly incorporated herein by reference.

CROSS REFERENCE

Cross reference is made to each of U.S. patent application Ser. No. 13/630,935, now U.S. Pat. No. 9,855,065, entitled "ORTHOPAEDIC SURGICAL INSTRUMENT SYSTEM FOR IMPLANTING A PROSTHETIC PATELLA COMPONENT" by Jennifer B. Clever et al.; U.S. patent application Ser. No. 13/630,951, now U.S. Pat. No. 9,554,813, entitled "PATELLA DRILL GUIDE AND TRIAL SURGICAL INSTRUMENT" by Jennifer B. Clever et al.; and U.S. patent application Ser. No. 13/630,965, now U.S. Pat. No. 9,700,330, entitled "METHOD FOR SURGICALLY IMPLANTING A PROSTHETIC PATELLA COMPONENT" by Jennifer B. Clever et al. Each of these applications is assigned to the same assignee as the present application, and is hereby incorporated by reference.

TECHNICAL FIELD

The present disclosure relates generally to orthopaedic surgical instruments and, more particularly, to patella surgical instruments.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. In some cases, the knee prosthesis may also include a prosthetic patella component, which is secured to a posterior side of the patient's surgically-prepared patella.

SUMMARY

According to one aspect, an orthopaedic surgical instrument system includes a clamp having a first lever pivotally coupled to a second lever. A proximal end of the first lever includes an upper handle and a distal end of the first lever includes a retaining socket secured thereto. A proximal end of the second lever includes a lower handle and a distal end of the second lever includes a connector. The orthopaedic surgical instrument system also includes a patella drill guide and trial instrument having a connector configured to be selectively secured to the connector of the clamp. The patella drill guide and trial instrument also includes a posterior trial bearing surface configured to articulate with a condylar surface of a prosthetic femoral component. The patella drill guide and trial instrument also includes an anterior surface opposite the posterior trial bearing surface and having a number of spikes extending outwardly therefrom. The patella drill guide and trial instrument also includes a number of drill guide holes extending from the posterior trial bearing surface to the anterior surface. The orthopaedic surgical instrument system also includes a compression socket having connector configured to be selectively secured to the connector of the clamp in place of the patella drill guide and trial instrument. The compression socket has a receptacle defined in an anterior surface. The orthopaedic surgical instrument system also includes a number of compressible bases configured to be selectively received in the receptacle of the compression socket. Each compressible base includes an anterior surface having a different shape from every other compressible base. Each compressible base is formed from a deformable material such as, for example, a compression material.

In some embodiments, the number of compressible bases include a first compressible base. The anterior surface of the first compressible base includes a circular rim and a concavely curved surface extending inwardly from the circular rim.

In some embodiments, the circular rim of the first compressible base has a medial width and a lateral width that is greater than the medial width.

In some embodiments, the first compressible base has a medial thickness and a lateral thickness that is greater than the medial thickness.

In some embodiments, the circular rim of the first compressible base includes a lateral section that defines a first imaginary plane and a medial section that defines a second imaginary plane, and a non-zero angle is defined between the first imaginary plane and the second imaginary plane.

In some embodiments, the number of compressible bases include a second compressible base that includes a body, a medial wedge extending anteriorly from the body, and a lateral wedge extending anteriorly from the body. The medial wedge and the lateral wedge cooperate to define the anterior surface of the second compressible base.

In some embodiments, the medial wedge is connected to the lateral wedge to define an oblong shape.

In some embodiments, the medial wedge includes a concavely curved anterior surface that defines a portion of the anterior surface of the second compressible base.

In some embodiments, the lateral wedge includes a convexly curved anterior surface that defines a second portion of the anterior surface of the second compressible base.

In some embodiments, the medial wedge has a maximum thickness, and the lateral wedge has a maximum thickness greater than the maximum thickness of the medial wedge.

In some embodiments, the compression socket includes an annular flange configured to selectively engage and retain each compressible base in the receptacle.

In some embodiments, each compressible base includes a posteriorly-extending tab to orient the compressible base in the receptacle of the compression socket.

In some embodiments, the compression socket comprises a ring having the receptacle and a connecting slot formed therein. The connector of the clamp includes a connecting tongue configured to be received into the connecting slot of the compression socket so as to secure the compression socket to the clamp.

According to another aspect, an orthopaedic surgical instrument system includes a clamp having a first lever pivotally coupled to a second lever. A proximal end of the first lever includes an upper handle and a distal end of the first lever includes a retaining socket secured thereto. A proximal end of the second lever includes a lower handle and a distal end of the second lever includes a connector. The orthopaedic surgical instrument system also includes a patella drill guide and trial instrument having a connector configured to be selectively secured to the connector of the clamp. The patella drill guide and trial instrument also includes a posterior trial bearing surface configured to articulate with a condylar surface of a prosthetic femoral component. The patella drill guide and trial instrument also includes an anterior surface opposite the posterior trial bearing surface and having a number of spikes extending outwardly therefrom. The patella drill guide and trial instrument also includes a number of drill guide holes extending from the posterior trial bearing surface to the anterior surface. The orthopaedic surgical instrument system also includes a compression socket having connector configured to be selectively secured to the connector of the clamp in place of the patella drill guide and trial instrument. The compression socket has a receptacle defined in an anterior surface. The orthopaedic surgical instrument system also includes a compressible base, selected from a number of compressible bases, configured to be selectively received in the receptacle of the compression socket. The second lever includes a plurality of teeth. The first lever includes a pawl having one end pivotably coupled to the first lever. The pawl is configured for slidable engagement with a spring-loaded member of a button such that positioning the button in a first position engages the pawl with the pawl teeth, and sliding the button in a second position disengages the pawl with the teeth.

In some embodiments, the pawl includes a lower surface from which extends a number of pawl teeth for selective engagement with the teeth of the second lever, the pawl teeth being position on another end of the pawl.

In some embodiments, the pawl includes a pawl release extending from the another end of the pawl for manually releasing the pawl in the event of jamming.

In some embodiments, the pawl release is configured to receive an upward force on a lower surface thereof for manually pivoting the pawl such that the pawl teeth disengage the teeth of the second lever.

According to one aspect, a method of performing an orthopaedic surgical procedure on a patella of a patient, includes resecting the patella of the patient to produce a generally planar resected patellar surface, positioning a patella drill guide and trial instrument on the resected patellar surface. The patella drill guide and trial instrument having a posterior trial bearing surface configured to articulate with a condylar surface of a prosthetic femoral component, and a number of drill guide holes formed in the posterior trial bearing surface. The number of drill guide holes extends through the patella drill guide and trial instrument. The method further includes trialing the patellofemoral joint with the patella drill guide and trial instrument positioned on the resected patellar surface. The method further includes advancing a drill through the number of drill guide holes formed in the posterior trial bearing surface of the patella drill guide and trial instrument and into the resected patellar surface so as to drill a number of anchor holes in the patella of the patient subsequent to trialing the patellofemoral joint. The method further includes selecting a patella component from a group consisting of a dome patella component and an anatomic patella component. The method further includes selecting a compressible base from a number of compressible bases having differently-shaped anterior surfaces from each other, an anterior surface of the selected compressible base being shaped to correspond to the selected patella component. The method further includes securing the selected compressible base to a compression socket, securing the compression socket to a removable clamp, positioning the selected compression socket into contact with the selected patella component, and operating the removable clamp to clamp the patella component to the patella of the patient.

In some embodiments, the method further includes securing the removable clamp to the patella drill guide and trial instrument subsequent to trialing the patellofemoral joint, but prior to advancing the drill through the number of drill guide holes formed in the posterior trial bearing surface of the patella drill guide and trial instrument to drill the number of anchor holes in the patella of the patient.

BRIEF DESCRIPTION OF THE DRAWINGS

The detailed description particularly refers to the following figures, in which.

DETAILED DESCRIPTION OF THE DRAWINGS

Figure 1:
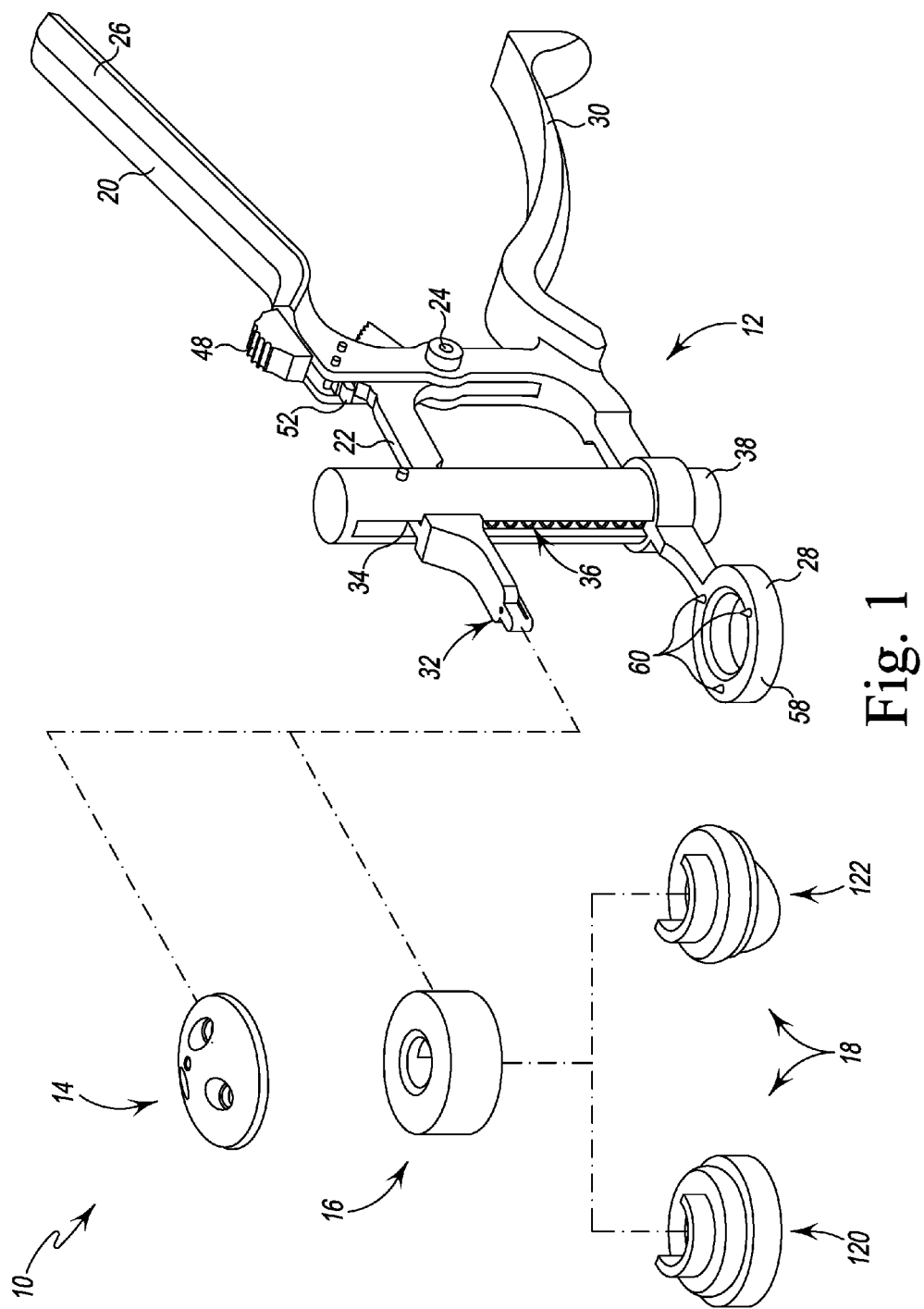
FIG. 1 is a perspective view of an orthopaedic surgical instrument system showing the clamp, the patella drill guide and trial instrument, and the compressible bases, in exploded arrangement.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring to FIG. 1, an orthopaedic surgical instrument system 10 includes a removable patella clamp 12, a patella drill guide and trial instrument 14 configured to be secured to the patella clamp 12, and a compression socket 16 configured to be secured to the patella clamp 12 in place of the trial instrument 14. As described in greater detail below, the instrument system 10 is utilized to surgically prepare a patient's patella 300 for implantation of a prosthetic patella component 302 (see FIGS. 18 and 21). To do so, the patella drill guide and trial instrument 14 may be used as both a trial instrument to trial the patellofemoral joint and as a drill guide to drill anchor holes into the planar, resected posterior surface of the patient's patella 300. The surgeon may also use the patella drill guide and trial instrument 14 to size and select a patella prosthetic component suitable for use with the particular patient's patella. The surgeon may then attach the compression socket 16 to the patella clamp 12 with one of the compressible bases 18 corresponding to the selected patella prosthetic component to secure the prosthetic component to the patient's patella.

Figure 2:
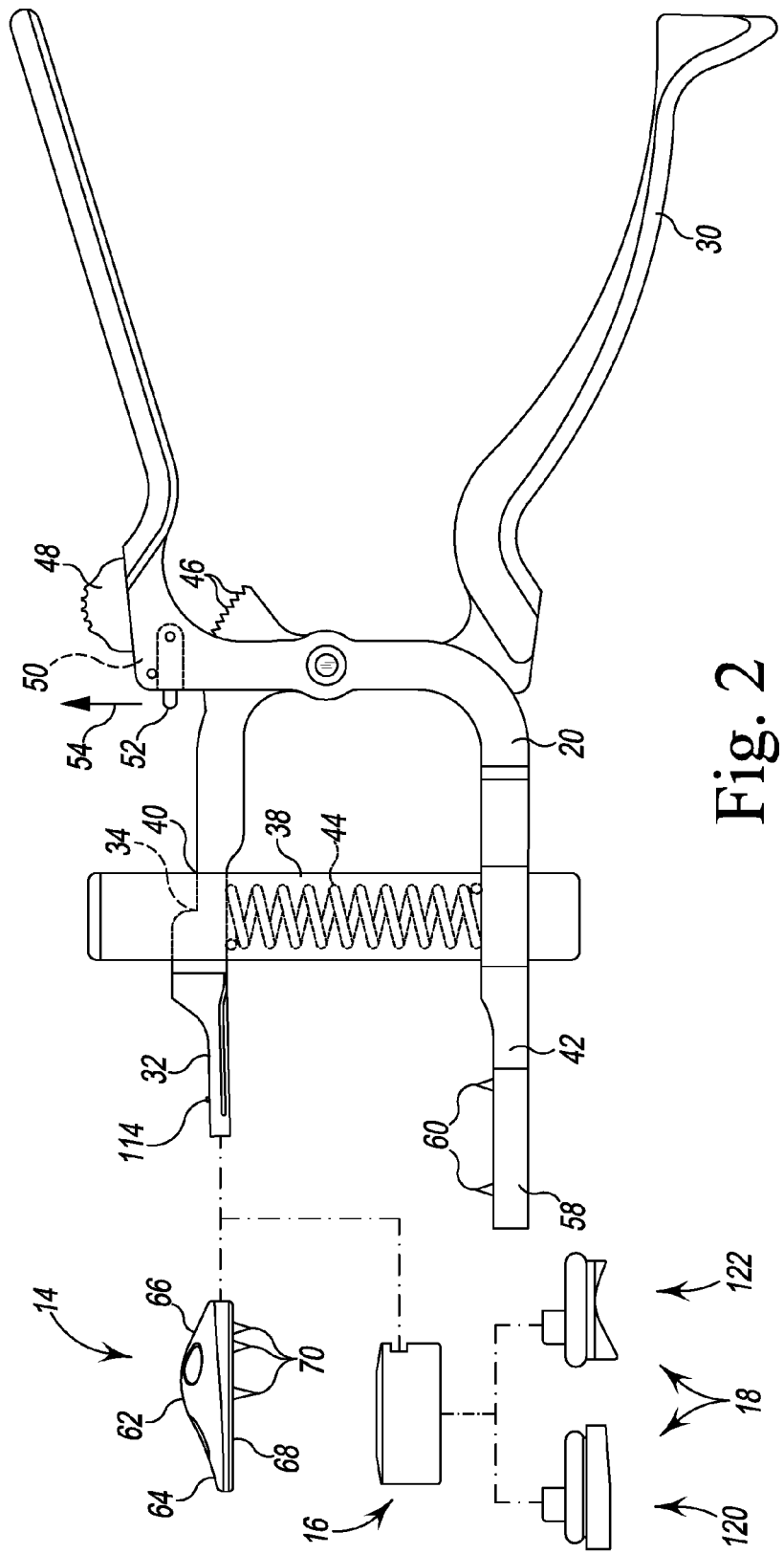
FIG. 2 is side elevation view of the system of FIG. 1.

As shown in FIG. 1, the patella clamp 12 of the instrument system 10 includes a pair of levers 20, 22 pivoted together with a pivot pin 24. The proximal end of the lever 20 includes an upper handle 26, with the distal end of the lever 20 having a retaining socket 28. The proximal end of the lever 22 includes a lower handle 30, with the distal end of the lever 22 having a connector 32. The lever 22 is modular in design in that the connector 32 is not integrally formed with the lower handle 30. A proximal end 34 of the connector 32 is captured in a slot 36 formed in a cylinder housing 38. As shown in FIG. 2, the proximal end 34 of the connector 32 is coupled to the distal end 40 of the lower handle 30 within the cylinder housing 38 such that the connector 32 is maintained in substantially parallel relationship with the distal end 42 of the lever 20 as it translates upwardly and downwardly within the cylinder housing 38. A compression spring 44 is positioned in the cylinder housing 38 and exerts a spring bias on the proximal end 34 of the connector 32 so as to urge the connector 32 in a direction away from the retaining socket 28.

When a surgeon squeezes or otherwise urges the two handles 26, 30 toward one another, the levers 20, 22 pivot about the pin 24 thereby causing the connector 32 and the retaining socket 28 to move toward one another. When the surgeon releases the two handles 26, 30, the spring bias of the compression spring 44 urges the connector 32 away from the retaining socket 28 thereby causing the levers 20, 22 to pivot about the pin 24 so as to move the two handles 26, 30 away from one another.

As can be seen in FIG. 2, the lever 22 has a number of ratchet teeth 46 formed therein. A button 48 is secured to the lever 20 near its upper handle 26. The button 48 engages a locking pawl 50 such that the locking pawl 50 is moved into engagement with the ratchet teeth 46 by sliding the button 48 in a direction toward the cylinder housing 38, and disengaged from the ratchet teeth 46 by sliding it in the opposite direction. When the locking pawl 50 engages ratchet teeth 46, the levers 20, 22 of the patella clamp 12 are locked and therefore prevented from moving relative to one another. When the locking pawl 50 is disengaged from the ratchet teeth 46, the levers 20, 22 of the patella clamp 12 are free to move relative to one another.

In the illustrative embodiment, the locking pawl 50 includes a flange 52 that extends outwardly from lever 20. The flange 52 is sized such that a surgeon or other user may pull on the flange 52 in the direction indicated by arrow 54 to manually release the locking pawl 50 in the event of, for example, jamming, which may occur when too much pressure is applied.

As can be seen in FIG. 1, in the illustrative embodiment described herein, the clamp's retaining socket 28 is embodied as a ring 58 having a number of spikes 60 extending outwardly therefrom. The spikes 60 face toward a number of spikes of the patella drill guide and trial instrument 14 when the instrument 14 is secured to the clamp 12. In such an arrangement the clamp's spikes 60 cooperate with the spikes of the patella drill guide and trial instrument 14 to capture the patella 300 therebetween.

The patella clamp 12 may be constructed from a medical-grade metal such as stainless steel, cobalt chrome, or titanium, although other metals or alloys may be used.

Figure 3:
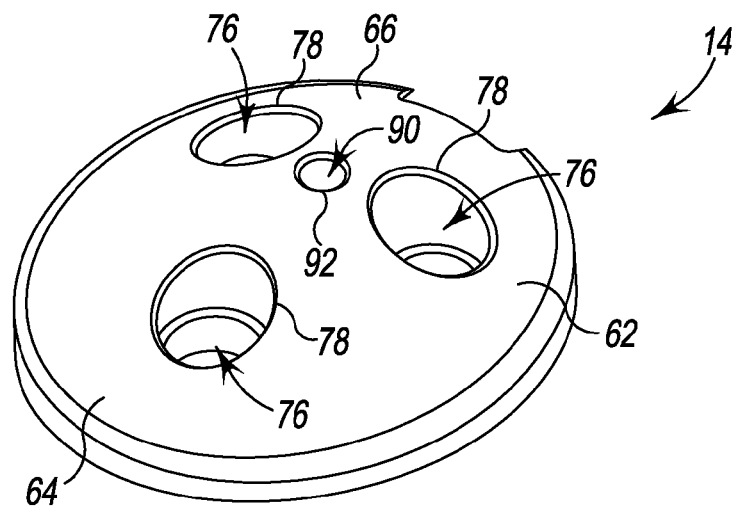
FIG. 3 is a perspective view of the patella drill guide and trial instrument of FIG. 1.
Figure 4:
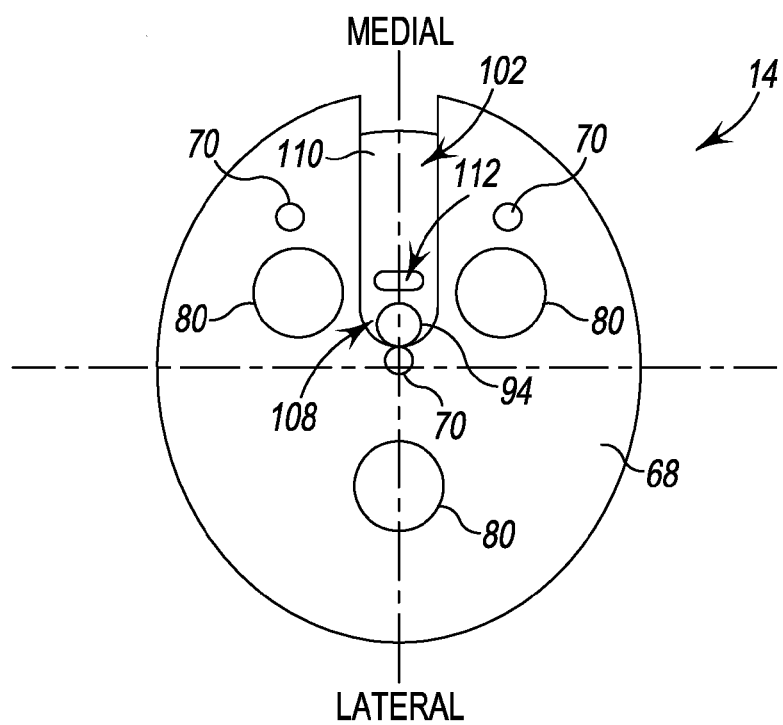
FIG. 4 is a plan view of the patella drill guide and trial instrument of FIG. 1.

Referring now to FIGS. 3-4, the patella drill guide and trial instrument 14 is shown in greater detail. As alluded to above, the patella drill guide and trial instrument 14 is used for fit assessment during a surgical procedure to implant the prosthetic patella component 302 into a patient's surgically-prepared patella 300. In essence, the patella drill guide and trial instrument 14 is used to ensure proper size selection of the ultimate patella component 302 (i.e., the patella component 302 that is ultimately implanted in the patient's patella 300). As will be discussed below in greater detail, the patella drill guide and trial instrument 14 also functions as a drill guide for guiding a drill bit used to drill the anchor holes in the patient's surgically-prepared patella 300 to receive the anchor pegs of the patella component 302.

Figure 19:
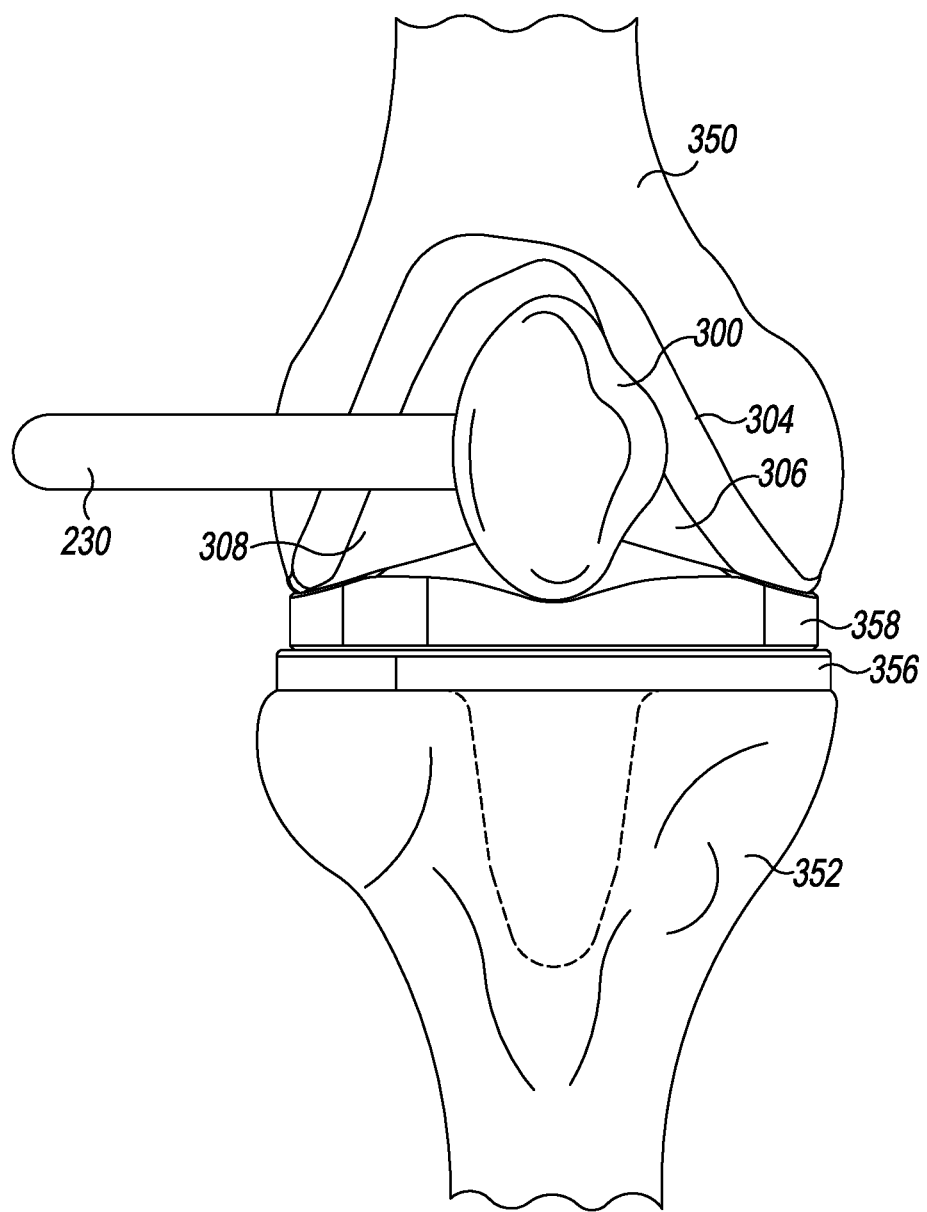
FIG. 19 is an anterior view of the knee of a patient during trialing.

As shown in FIG. 3, the patella drill guide and trial instrument 14 includes a posterior trial bearing surface 62 in the form of a curved peak surface configured to articulate with the condylar surface of the a prosthetic femoral component 304 (see FIG. 19). In particular, the posterior trial bearing surface 62 of the patella drill guide and trial instrument 14 includes a lateral trial articular surface 64 and a medial trial articular surface 66. The trial articular surfaces 64, 66 are configured to articulate with a lateral condyle surface 306 and a medial condyle surface 308, respectively, of the femoral component 304. The femoral component 304 is configured to emulate the configuration of the patient's natural femoral condyles, and, as such, the lateral condyle surface 306 and the medial condyle surface 308 are configured (e.g., curved) in a manner which mimics the condyles of the natural femur. The lateral condyle surface 306 and the medial condyle surface 308 are spaced apart from one another thereby defining a trochlear groove 310 therebetween.

As can be seen in FIG. 4, the patella drill guide and trial instrument 14 also includes a flat anterior surface 68 having a number of fixation members, such as spikes 70, extending anteriorly away therefrom. The spikes 70 are configured to be inserted into a surgically prepared posterior surface of the patient's natural patella (not shown). In such a way, the posterior trial bearing surface 62 of the patella drill guide and trial instrument 14 faces toward the femoral component 304 thereby allowing the posterior trial bearing surface 62 to articulate with the femoral condyle surfaces 306, 308 during flexion and extension of the patient's knee during a patellofemoral trialing procedure.

The patella drill guide and trial instrument's body has a number of drill guide holes 76 formed therein. The drill guide holes 76 extend throughout the entire thickness of the patella drill guide and trial instrument's body. That is, a posterior end 78 of the drill guide holes 76 opens into the posterior trial bearing surface 62 of the patella drill guide and trial instrument 14, with the opposite anterior end 80 of the drill guide holes 76 opening into the instrument's anterior surface 66. The guide holes 76 function as drill guides for guiding a drill bit 84 (see FIG. 20) used to drill the anchor holes in the patient's surgically-prepared patella 300 to receive the anchor pegs of the patella component 302. As such, the size and position of each of the drill guide holes 76 coincides with the size and position of the anchor pegs (not shown) of the patella component 302.

As shown in FIGS. 3-4, the patella drill guide and trial instrument 14 has an alignment bore 90 formed therein. Like the drill guide holes 76, the alignment bore 90 extends throughout the entire thickness of the patella drill guide and trial instrument's body. That is, a posterior end 92 of the alignment bore 90 opens into the posterior trial bearing surface 62 of the patella drill guide and trial instrument 14, with the opposite anterior end 94 of the alignment bore 90 opening into a slot 102 of the instrument's connector. In the illustrative embodiment, the alignment bore 90 functions as a visual alignment guide that allows the surgeon to align the apex of the patella drill guide and trial instrument 14 with the former location of the apex of the patient's natural patella 300 prior to resection of the patella 300.

Figure 14:
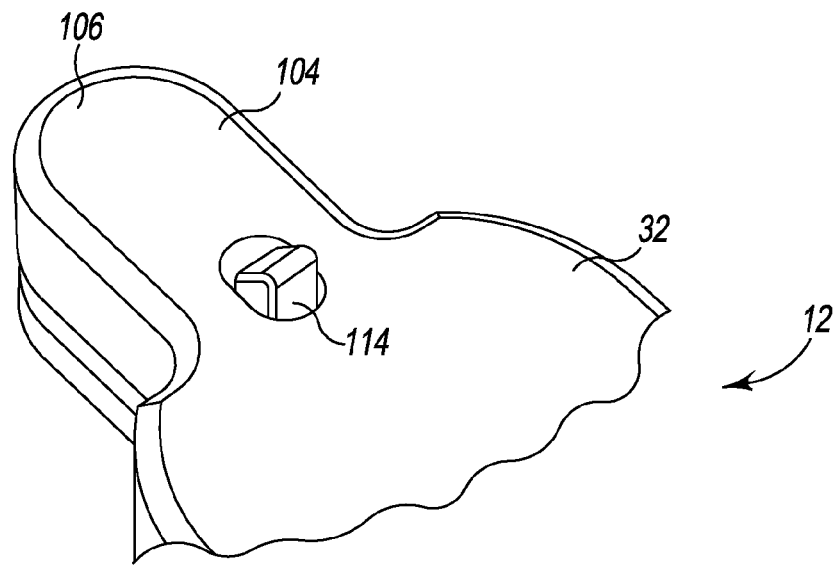
FIG. 14 is a perspective view of the connector of the clamp.
Figure 15:
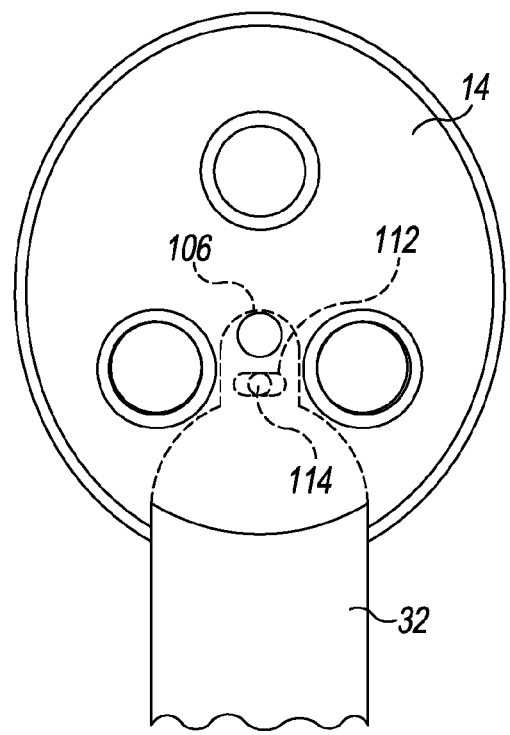
FIG. 15 is a plan view of the clamp attached to the patella drill guide and trial instrument.

As alluded to above, the patella drill guide and trial instrument 14 may be selectively secured to the removable patella clamp 12. In that regard, the patella drill guide and trial instrument 14 includes a female connector geometry configured to receive the male geometry of the connector 32 of the patella clamp 12 (see FIG. 14). Specifically, the body of the patella drill guide and trial instrument 14 has a connecting slot 102 formed therein. As shown in FIG. 4, the connecting slot 102 is positioned between the posterior trial bearing surface 62 and the anterior surface 68. The connecting slot 102 is shaped and sized to receive a connecting tongue 104 of the patella clamp's connector 32. As shown in FIG. 14, the connecting tongue 104 includes a tip 106 which extends outwardly from a rounded surface of the main body of the connector 32. As can be seen in FIG. 4, the connecting slot 102 of the patella drill guide and trial instrument 14 has a similar shape, including a tip recess 108 that is sized and shaped to receive the tip 106 of the patella clamp's connecting tongue 104.

As shown in FIG. 4, the upper sidewall 110 that defines the upper surface of the connecting slot 102 has a locking recess 112 defined therein. In the exemplary embodiment described herein, the locking recess 112 is generally oblong in shape. The locking recess 112 is sized and positioned to receive a locking mechanism of the patella clamp's connector 32 to secure the patella clamp 12 to the patella drill guide and trial instrument 14. In an embodiment, the locking mechanism is embodied as a leaf-spring biased plunger 114 positioned on the tip 106 of the patella clamp's connecting tongue 104. As the patella clamp's connector 32 is inserted in the connecting slot, the plunger 114 is urged downwardly against its spring bias by the upper sidewall 110 until it reaches a position in which the plunger 114 is moved into the locking recess 112 by its spring bias. When the plunger 114 is positioned in the locking recess 112, the patella clamp 12 is firmly secured to the patella drill guide and trial instrument 14 until sufficient force is applied to pull the two components apart by urging the plunger 114 downwardly out of the locking recess 112 to allow the patella clamp 12 to be separated from the patella drill guide and trial instrument 14.

In order to fit the needs of a given patient's anatomy, the patella drill guide and trial instrument 14 may be provided in a number of different sizes. For example, in the illustrative embodiment described herein, the patella drill guide and trial instrument 14 may be embodied in five different medial/lateral lengths (e.g., 29 mm, 32 mm, 35 mm, 38 mm, and 41 mm) so as to mimic the various sizes of the prosthetic patella components 302. It should also be appreciated that in other embodiments the patella drill guide and trial instrument may be embodied to mimic other types of patella components. For example, the patella drill guide and trial instrument may be embodied to mimic "conforming" or "anatomic" patella components (see FIG. 18), which are designed to conform with the condylar surfaces of the femur.

In the exemplary embodiment described herein, the patella drill guide and trial instrument 14 is embodied as a monolithic metal body constructed with a biocompatible metal that allows for smooth articulation between the patella drill guide and trial instrument 14 and the femoral component 304. Examples of such biocompatible metals include stainless steel, cobalt chrome, or titanium, although other metals or alloys may be used. The patella drill guide and trial instrument 14 may also be embodied as a monolithic polymer trial instrument. As such, the patella drill guide and trial instrument 14 may be made of any suitable medical-grade polymeric material. Examples of such polymeric materials include polyetheretherketone (PEEK), ultrahigh molecular weight polyethylene (UHMWPE), or acetal. In such an embodiment, the monolithic polymer trial may include metallic inserts (e.g., sleeves) positioned in the drill guide holes 76.

Referring now to FIGS. 5-13, the removable clamp 12 may also be secured to a compression socket 16, which is configured to be selectively coupled to one of a number of compressible bases 18. The bases 18 and the socket 16 may be used to assert clamping pressure on the patella component 302 as it is cemented in place on the patient's resected patella 300. Each compressible base 18 is formed of a deformable material and functions to engage the posterior bearing surface 312 of the patella component 302. As described in greater detail below, the compressible bases 18 include a dome patella base 120 shaped to engage a dome-shaped patella prosthetic component 314 (see FIG. 18) and an anatomic base 122 shaped to engage an anatomic patella prosthetic component 316 (see FIG. 18).

Figure 5:
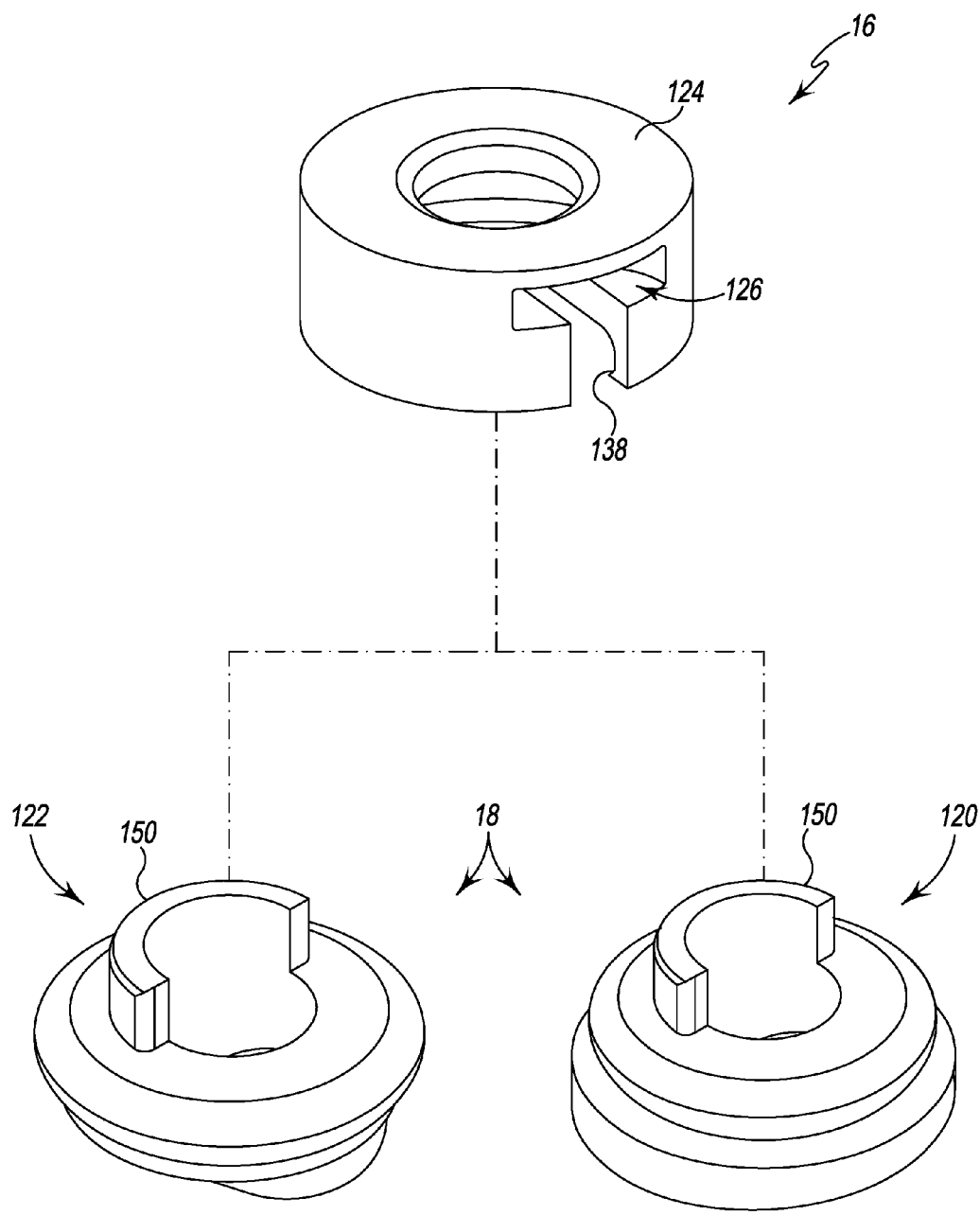
FIG. 5 is an exploded perspective view of the compression socket and compressible bases.

As shown in FIG. 5, the compression socket 16 includes a body 124 that is the form of a ring. The body 124 of the compression socket 16 may be embodied as a monolithic metal body constructed with a biocompatible such as stainless steel, cobalt chrome, or titanium, although other metals or alloys may be used. The body 124 may also be embodied as a monolithic polymer trial instrument constructed with any suitable medical-grade polymeric material such as polyetheretherketone (PEEK), ultrahigh molecular weight polyethylene (UHMWPE), or acetal. The compressible bases 18 may be constructed with any suitable medical-grade compressible material such as an elastomeric material. In the illustrative embodiment, each of the bases 18 is formed from silicone.

In order to fit the needs of a given patient's anatomy, the compressible bases 18 and/or socket 16 may be provided in a number of different sizes. For example, in the illustrative embodiment described herein, the compressible bases 18 and/or socket 16 may be embodied in five different medial/lateral lengths (e.g., 29 mm, 32 mm, 35 mm, 38 mm, and 41 mm) so as to mimic the various sizes of the prosthetic patella components 302.

Figure 6:
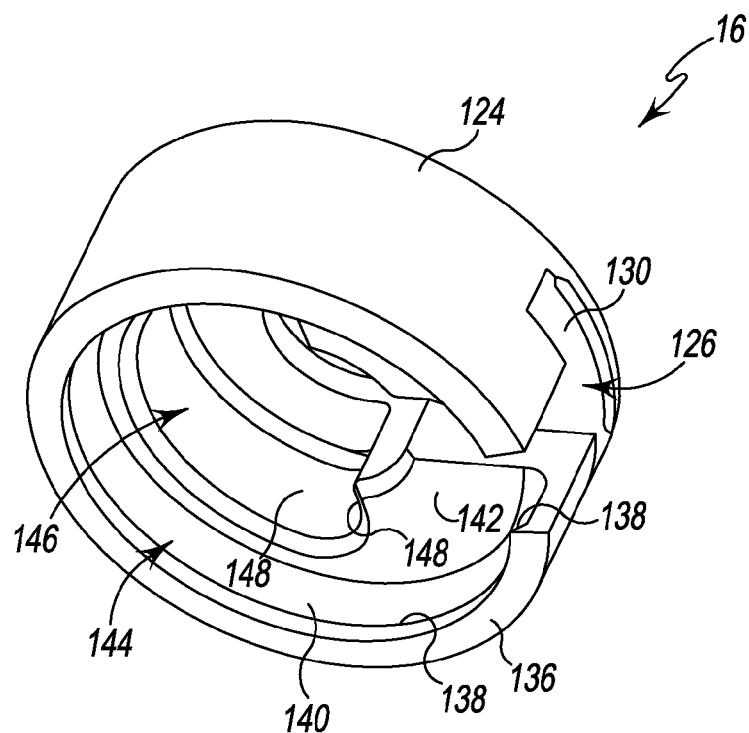
FIG. 6 is a bottom perspective view of the compression socket.
Figure 7:
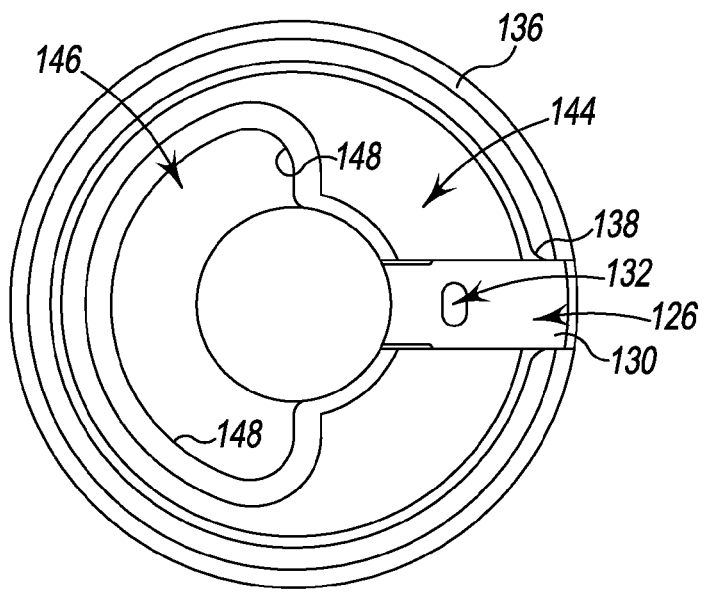
FIG. 7 is a bottom plan view of the compression socket.

The compression socket 16 includes a female connector geometry that is similar to that of the patella drill guide and trial instrument 14 and, as a result, configured to receive the male geometry of the connector 32 of the patella clamp 12. Specifically, the body 124 of the compression socket 16 has a connecting slot 126 formed therein. As shown in FIGS. 5-7, the connecting slot 126 is shaped and sized to receive the connecting tongue 104 of the patella clamp's connector 32. The upper sidewall 130 that defines the upper surface of the connecting slot 126 has a locking recess 132 defined therein. In the exemplary embodiment described herein, the locking recess 132 is generally oblong in shape. The locking recess 112 is sized and positioned to receive the plunger 114 of the patella clamp 12. As the patella clamp's connector 32 is inserted in the connecting slot 126, the plunger 114 is urged downwardly against its spring bias by the upper sidewall 130 until it reaches a position in which the plunger 114 is moved into the locking recess 132 by its spring bias. When the plunger 114 is positioned in the locking recess 132, the patella clamp 12 is firmly secured to the compression socket 16 until sufficient force is applied to pull the two components apart by urging the plunger 114 downwardly out of the locking recess 112 to allow the patella clamp 12 to be separated from the compression socket 16.

As shown in FIG. 6, the socket body 124 has an opening 134 defined in its anterior surface 136. The opening 134 is defined by an annular flange 138 that extends inwardly from an inner wall 140 of the socket body 124. The inner wall 140 cooperates with an anterior wall 142 of the socket body 124 to define a receptacle 144 that is sized to selectively receive any of the bases 18. The receptacle 144 includes an orientation slot or groove 146 is defined in the anterior wall 142. In the illustrative embodiment, the groove 146 is defined by a number of shaped walls 148 that correspond to the shape of the orientation tab 150 of each base 18. As described in greater detail, the groove 146 cooperates with the tab 150 to ensure that each base 18 is attached to the socket body 124 in its proper orientation.

Figure 9:
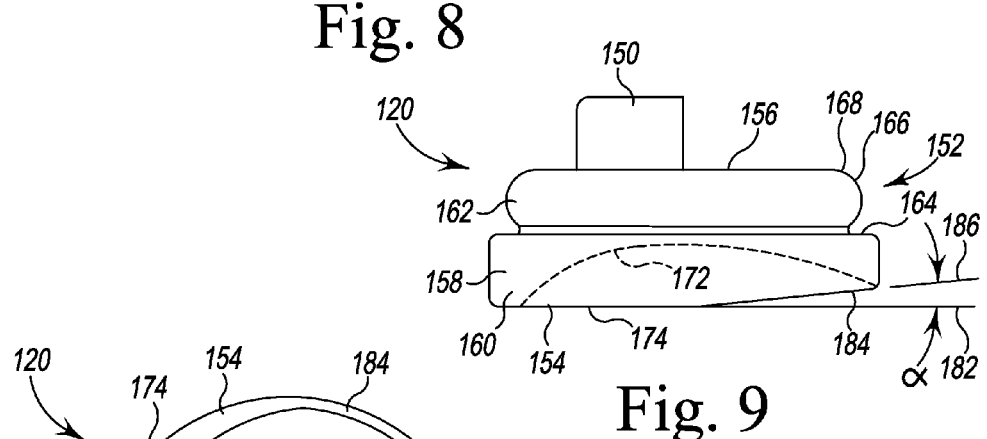
FIG. 9 is an elevation view of the first compressible base of the system of FIG. 1.
Figure 18:
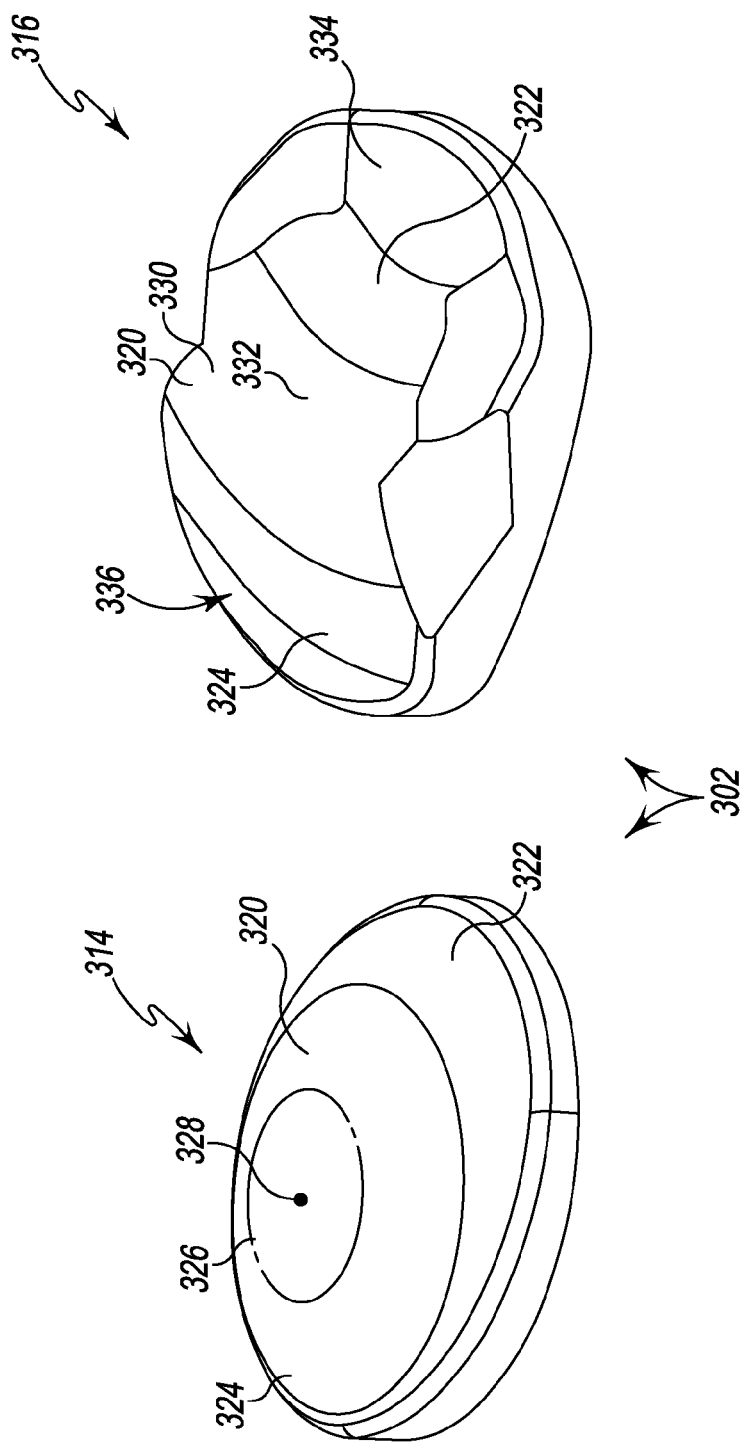
FIG. 18 is a perspective view of a dome patella implant and an anatomical patella implant.

As described above, the compressible bases 18 include a dome patella base 120 shaped to engage a dome-shaped patella prosthetic component 314 (see FIG. 18). In the illustrative embodiment, the dome patella base 120 includes a ring-shaped body 152 that has an anterior surface 154 positioned opposite a posterior surface 156. As shown in FIG. 9, the orientation tab 150 extends outwardly from the posterior surface 156. The body 152 includes a platform 158 having a cylindrical outer wall 160 that extends posteriorly from the anterior surface 154. The body 152 also includes a plug 162 extending from the posterior end 164 of the platform 158. The plug 162 includes an outer flange 166 that is configured to engage the annular flange 138 of the socket body 124 to retain the base 120 in the socket 16. In the illustrative embodiment, the outer flange 166 includes a curved outer surface 168.

Figure 8:
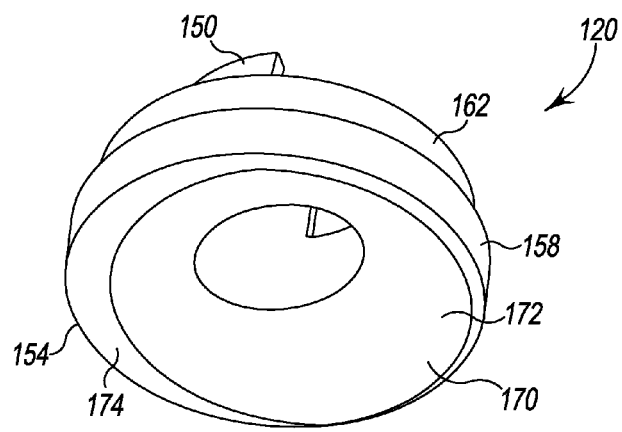
FIG. 8 is a bottom perspective view of the first compressible base of the system of FIG. 1.

As shown in FIG. 8, the anterior surface 154 of the compressible base 120 includes a rim 170 and a concavely curved surface 172 that extends inwardly from the rim 170. The curved surface 172 is shaped to receive the posterior surface 320 of the dome-shaped patella prosthetic component 314 (see FIG. 18). In the illustrative embodiment, the rim 170 has a circular outer edge but it should be appreciated that in other embodiments it may be oblong or oval.

Figure 10:
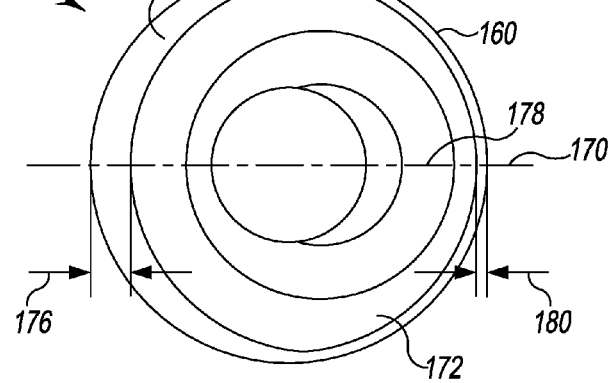
FIG. 10 is a bottom view of the first compressible base of the system of FIG. 1.

The rim 170 includes a crescent-shaped surface 174 that defines the lateral section of the rim 170. As shown in FIG. 10, the crescent-shaped surface 174 has a maximum width 176 defined along an imaginary line 178 extending in a medial-lateral direction. The width 176 is the lateral width of the rim 170. The medial width 180 of the rim 170 is also defined along the imaginary line 178. In the illustrative embodiment, the lateral width 176 is greater than the medial width 180. In that way, the dome patella base 120 is medialized, i.e., the concavely curved surface 172 is shifted toward the medial side of the base 120.

As shown in FIG. 9, the crescent-shaped surface 174 is substantially planar and defines an imaginary plane 182. The medial section 184 of the rim 170 extends at an angle relative to the surface 174 and defines another imaginary plane 186. In the illustrative embodiment, a non-zero angle α is defined between the planes 182, 186. As a result, the medial thickness of the base 120 is less than the lateral thickness.

Figure 11:
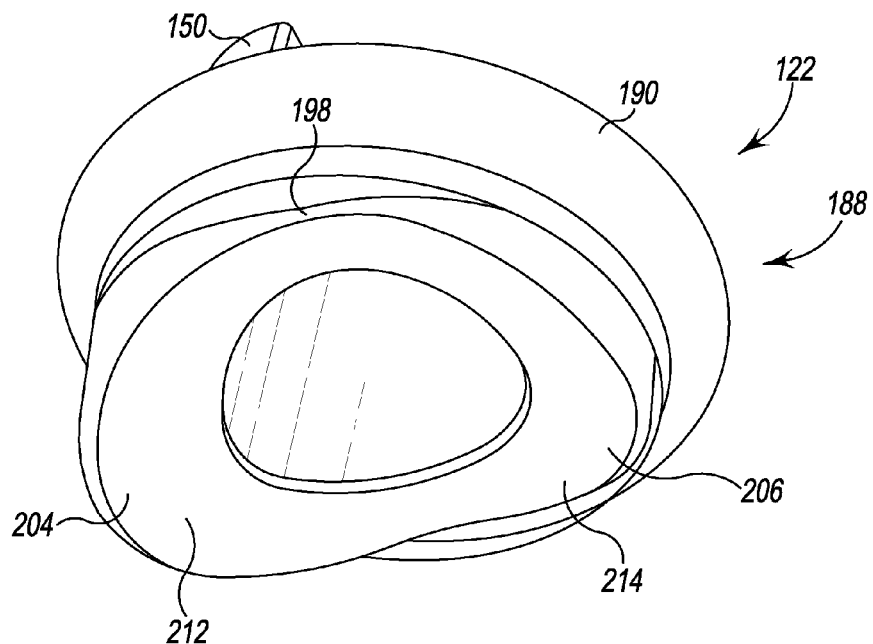
FIG. 11 is a bottom perspective view of the second compressible base of the system of FIG. 1.
Figure 12:
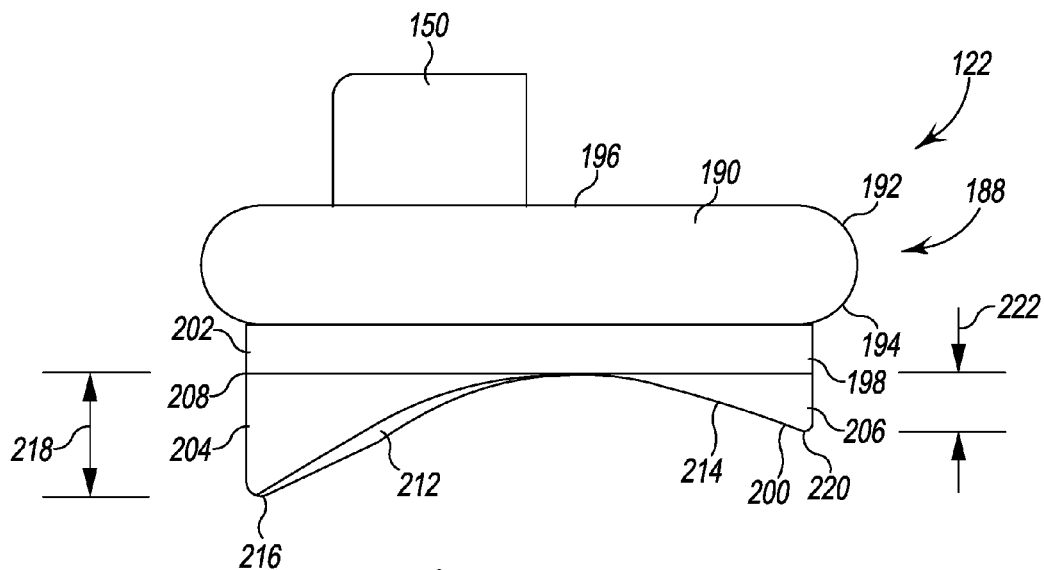
FIG. 12 is an elevation view of the second compressible base of the system of FIG. 1.

As described above, the compressible bases 18 include an anatomic base 122 shaped to engage an anatomic patella prosthetic component 316 (see FIG. 18). In the illustrative embodiment, the anatomic base 122 includes a ring-shaped body 188, as shown in FIGS. 11-12. The ring-shaped body 188 includes a plug 190 having an outer flange 192 that is configured to engage the annular flange 138 of the socket body 124 to retain the base 122 in the socket 16. In the illustrative embodiment, the outer flange 192 includes a curved outer surface 194.

The plug 190 includes a posterior surface 196, and the orientation tab 150 of the base 122 extends outwardly from the surface 196. The body 188 also includes a platform 198 that extends anteriorly from the plug 190. The platform 198 includes the anterior surface 200 of the anatomic base 122, which is shaped to engage an anatomic patella prosthetic component 316.

Figure 13:
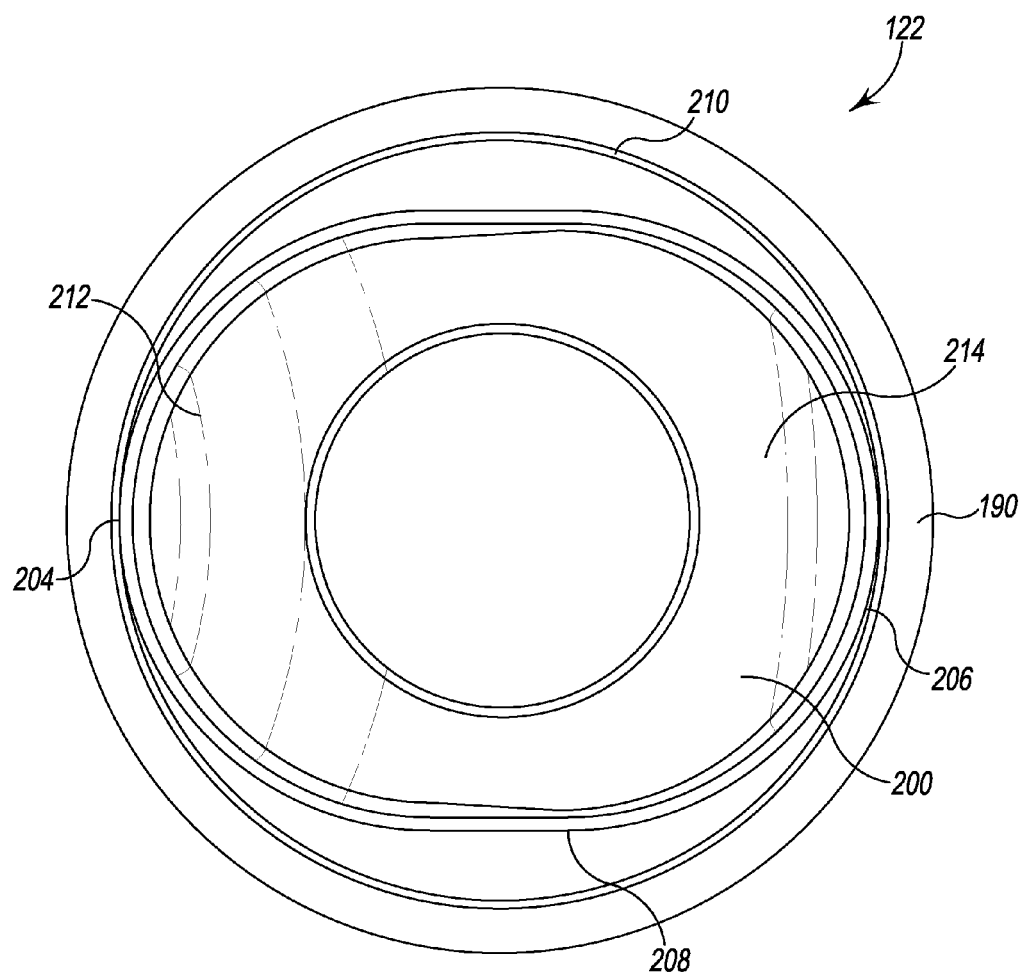
FIG. 13 is a bottom view of the second compressible base of the system of FIG. 1.

In the illustrative embodiment, the platform 198 is saddle-shaped and includes a connecting body 202, a lateral wedge 204 and a medial wedge 206 that extend anteriorly from the connecting body 202. The wedges 204, 206 cooperate to define the anterior surface 200 of the anatomic base 122. As shown in FIG. 13, the wedges 204, 206 are connected and define a posterior edge 208 that is illustratively an oblong shape. The connecting body 198, on the other hand, illustratively includes a circular-shaped outer wall 210.

In the illustrative embodiment, the configuration of the lateral wedge 204 is different from the configuration of the medial wedge 206. As shown in FIGS. 11-13, the lateral wedge 204 includes a convexly curved anterior surface 212 that defines one portion of the anterior surface 200 of the anatomic base 122. The medial wedge 206, on the other hand, includes a concavely curved surface 214 that defines another portion of the anterior surface 200 of the base 122. The shapes of the surfaces 212, 214 correspond to the shape of the posterior surface 320 of the anatomic patella prosthetic component 316, as described in greater detail below.

Returning to FIG. 12, the lateral wedge 204 extends to an anterior tip 216, and a maximum thickness 218 is defined between the tip 216 and the posterior edge 208 of the wedges 204, 206. Similarly, the medial wedge 206 extends to an anterior tip 220, and a maximum thickness 222 is defined between the tip 220 and the posterior edge 208 of the wedges 204, 206. As shown in FIG. 12, the thickness 218 is greater than the thickness 222.

Figure 16:
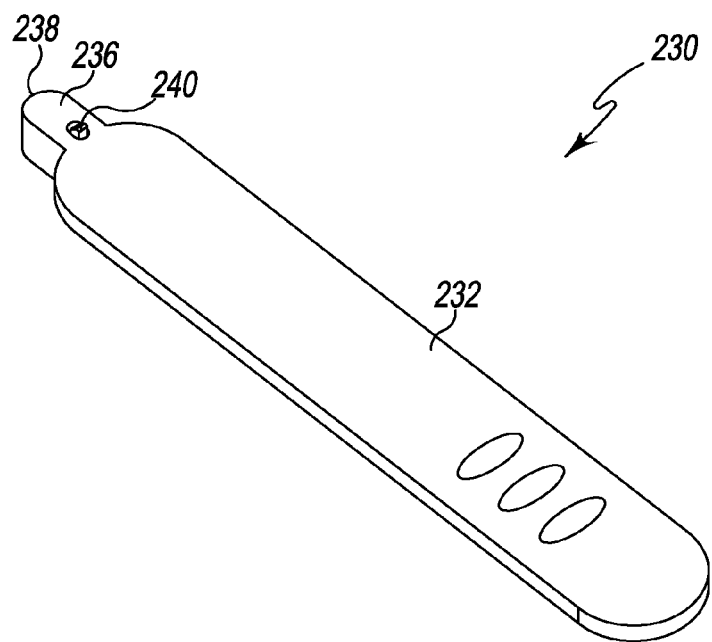
FIG. 16 a perspective view of the trial handle.
Figure 17:
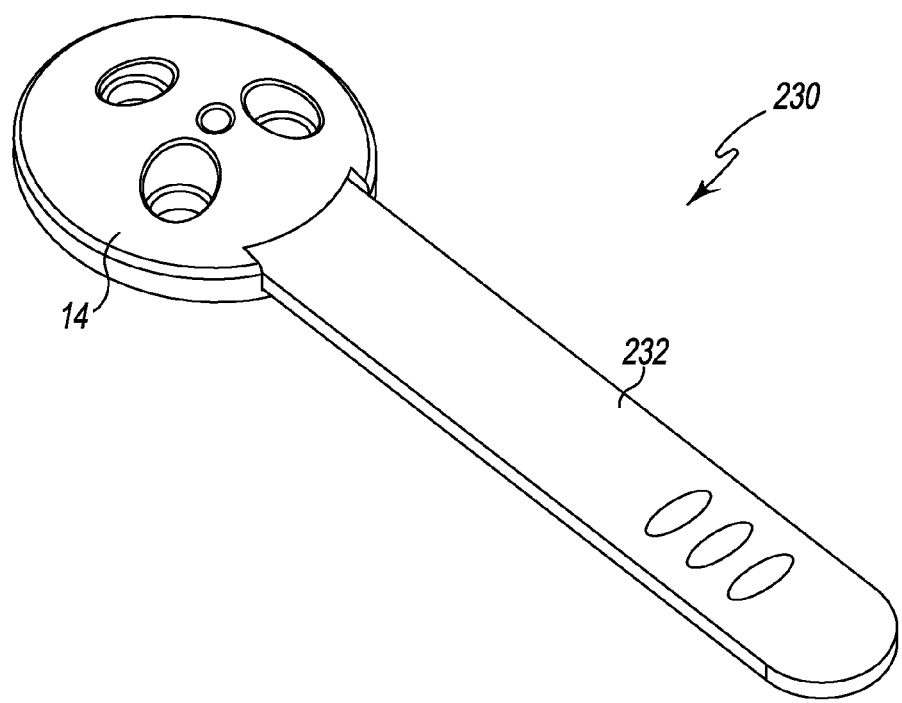
FIG. 17 is a perspective view of the trial handle inserted into the patella drill guide and trial instrument of FIG. 1.

As shown in FIGS. 16 and 17, the patella drill guide and trial instrument 14 may also be secured to an alignment handle 230. Use of the alignment handle 230 allows the surgeon to assess the rotational alignment of the patella drill guide and trial instrument 14 as it articulates in the trochlear groove 310 of the femoral component 304 during trialing of the patellofemoral joint. The alignment handle 230 includes a relatively flat elongated flange 232 having a connector 234 formed in one end thereof. The connector 234 of the alignment handle is identical to the patella clamp's connector 32 so as to mate with the connector of the patella drill guide and trial instrument 14 in an identical manner as the patella clamp 12. As such, the alignment handle's connector 234 has a connecting tongue 236 that includes a tip 238 which extends outwardly from a rounded surface of the main body of the connector 234. The connecting tongue 236 and its tip 238 are received into the connecting slot 102 of the patella drill guide and trial instrument 14 in a similar manner as the similar structures of the patella clamp's connector 32.

Likewise, the alignment handle's connector 234 includes a locking mechanism to secure the alignment handle 230 to the patella drill guide and trial instrument 14. In an embodiment, the locking mechanism is embodied as a biased plunger positioned on the tip 238 of the alignment handle's connector 234. In a specific embodiment, the biased plunger may be embodied as a leaf spring-biased plunger 240. The plunger 240 may be captured in the locking recess 112 of the connecting slot 102 of the patella drill guide and trial instrument 14 to firmly secure the alignment handle 230 to the patella drill guide and trial instrument 14 in an identical manner to as described above in regard to attachment of the patella clamp 12. The alignment handle 230 remains secured to the patella drill guide and trial instrument 14 by the plunger 240 until sufficient force is applied to pull the two components apart by urging the plunger 240 downwardly out of the locking recess 112 to allow the alignment handle 230 to be separated from the patella drill guide and trial instrument 14.

Referring now to FIG. 18, a pair of prosthetic patella components 302 of an implantable knee prosthesis are shown. The components 302 include a dome-shaped patella component 314 and an anatomic patella component 316. Both of the patella components 314, 316 include a posterior bearing surface 320 configured to articulate with the condylar surfaces of the femoral component 304. In particular, the posterior bearing surface 320 of the patella components 314, 316 includes a lateral articular surface 322 and a medial articular surface 324. The articular surfaces 322, 324 are configured to articulate with a lateral condyle surface 306 and a medial condyle surface 308, respectively, of the femoral component 304. Each of the components 314, 316 have a number of fixation members, such as pegs (not shown), extending away their respective anterior surfaces. The pegs are configured to be implanted into a surgically prepared posterior surface of the patient's natural patella (not shown). As described above, the instrument 14 may be used to drill holes in the patient's patella 300 sized and positioned to receive the pegs.

As shown in FIG. 18, the posterior surface 320 of the dome-shaped patella prosthetic component 314 is generally convex in shape and includes a curved peak surface 326 that defines the posterior-most point 328 of the component 314. In the illustrative embodiment, the point 328 is medialized. In that way, the lateral articular surface 322 is larger than the medial articular surface 324. The posterior surface 320 of the anatomic patella prosthetic component 316 also includes a curved peak surface 330 that defines the posterior-most point 332 of the component 316. In the illustrative embodiment, the point 332 is also medialized such that the lateral articular surface 322 is larger than the medial articular surface 324. Additionally, as shown in FIG. 18, the lateral articular surface 322 of the anatomic patella prosthetic component 316 includes a concave section 334 and the medial articular surface 324 includes a convex section 336.

Each of the patella components 314, 316 is embodied as a monolithic polymer body constructed with a material that allows for smooth articulation between the patella components 314, 316 and the femoral component 304. One such polymeric material is polyethylene such as ultrahigh molecular weight polyethylene (UHMWPE).

Figure 20:
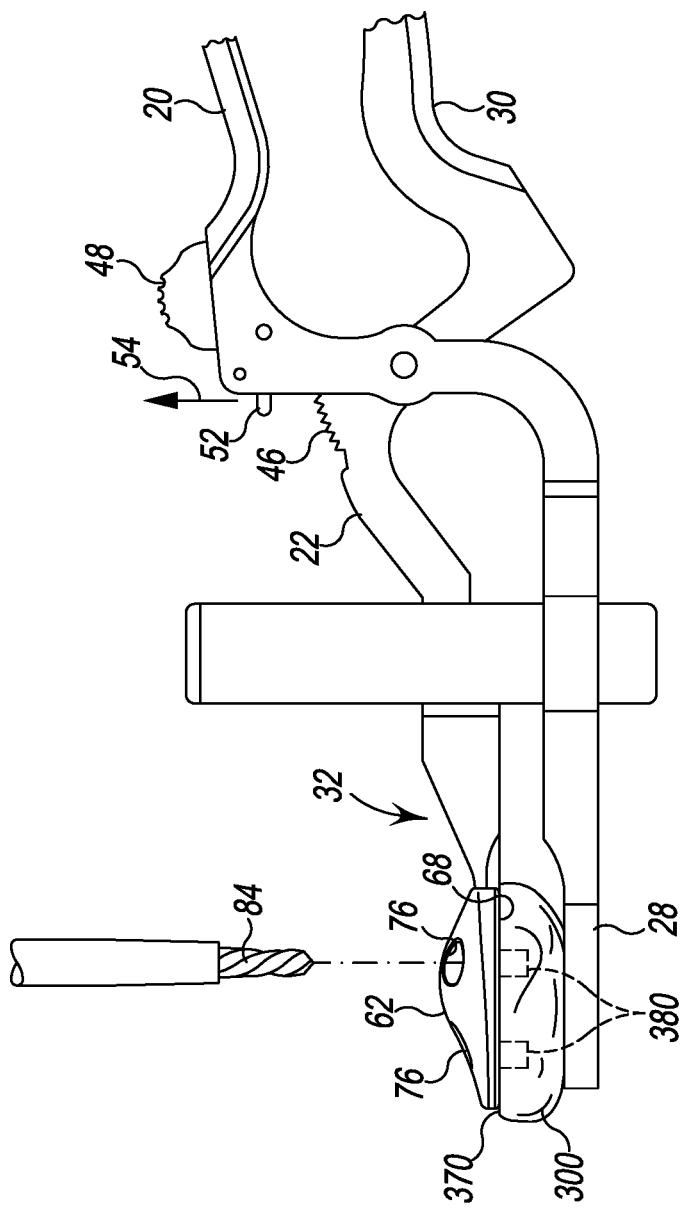
FIG. 20 is an elevation view of the system of FIG. 1 during drilling.
Figure 21:
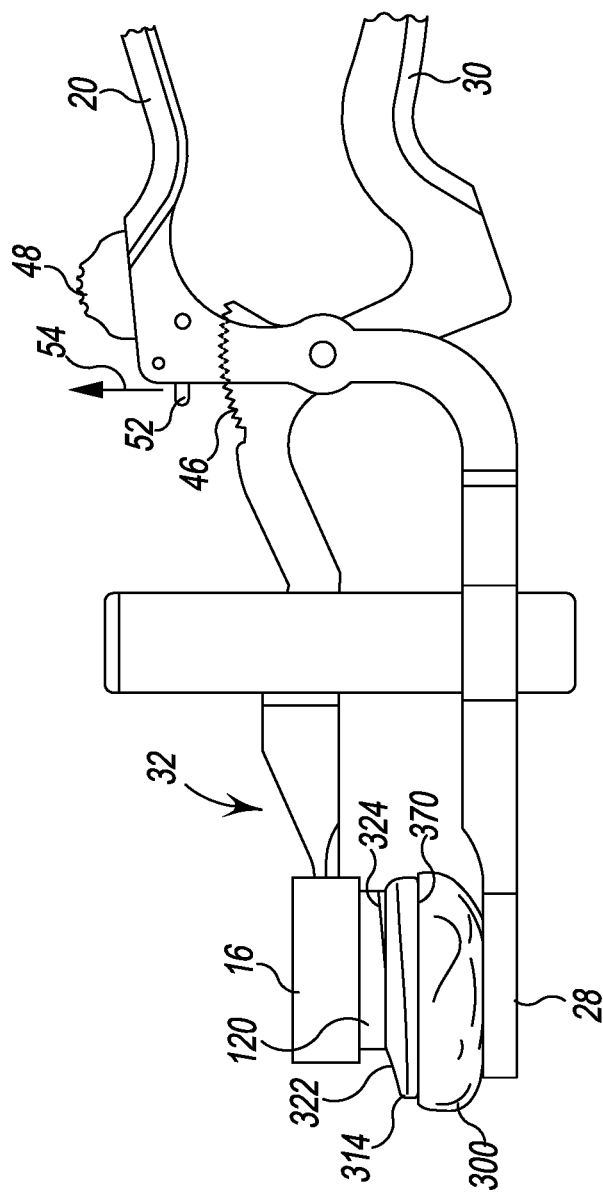
FIG. 21 is an elevation view of the system of FIG. 1 during clamping of the dome patella implant of FIG. 18.
Figure 22:
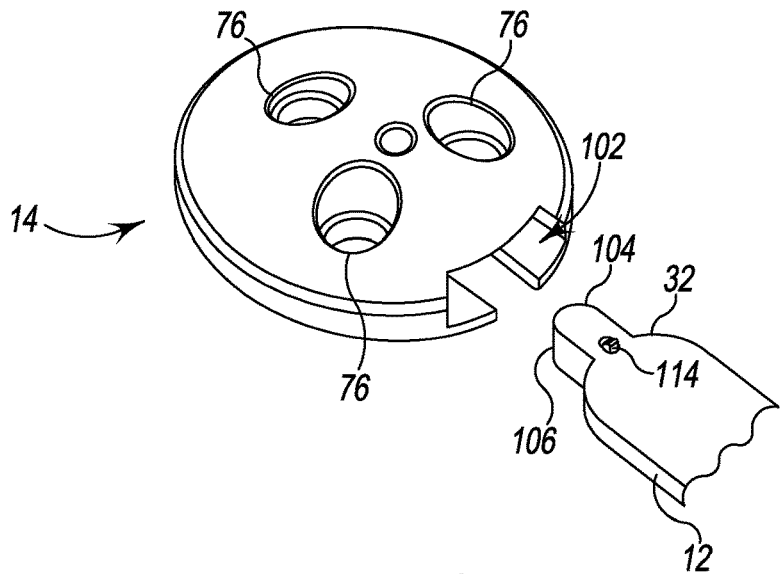
FIGS. 22-31 are additional illustrations of the system of FIG. 1.
Figure 23:
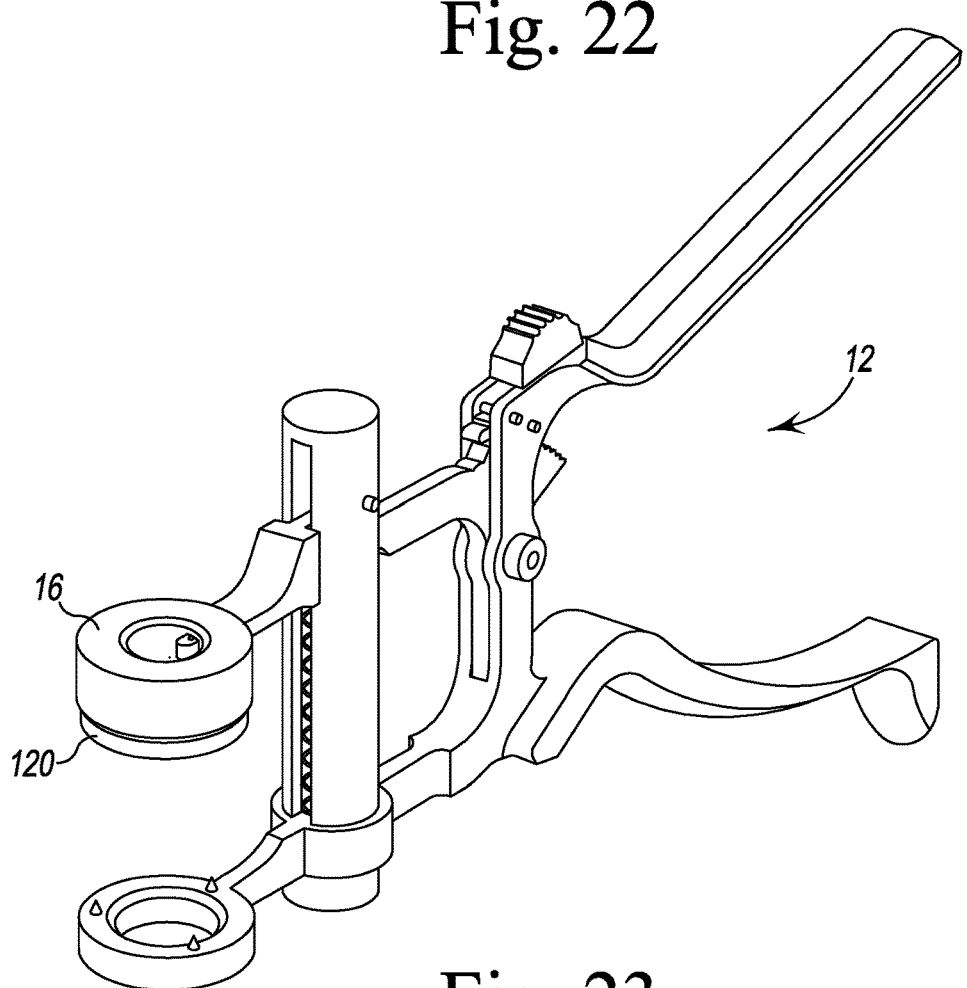
Figure 24:
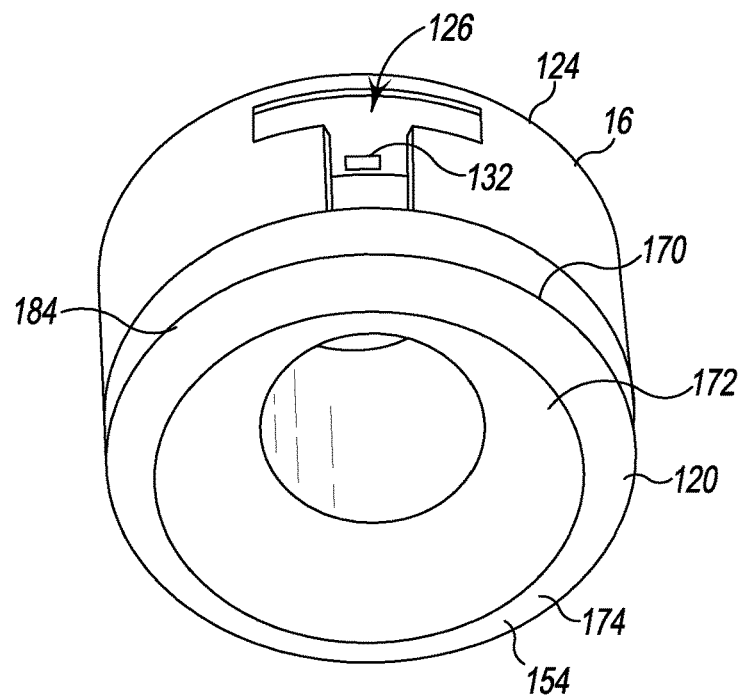
Figure 25:
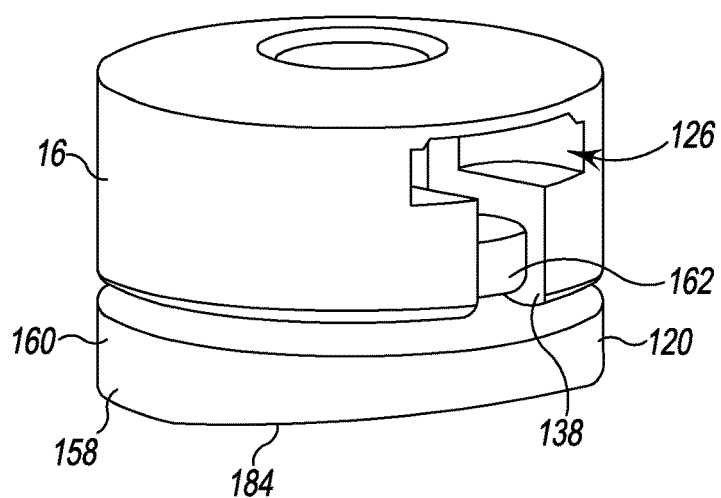
Figure 26:
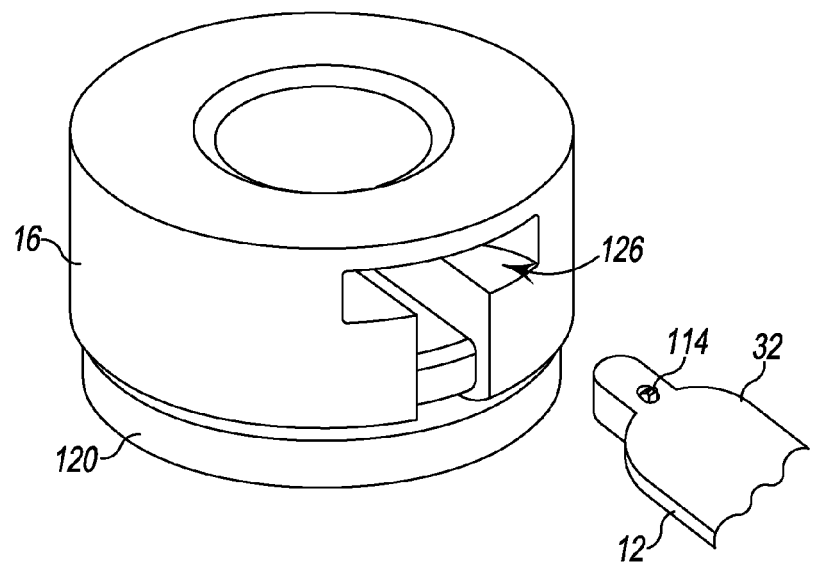
Figure 27:
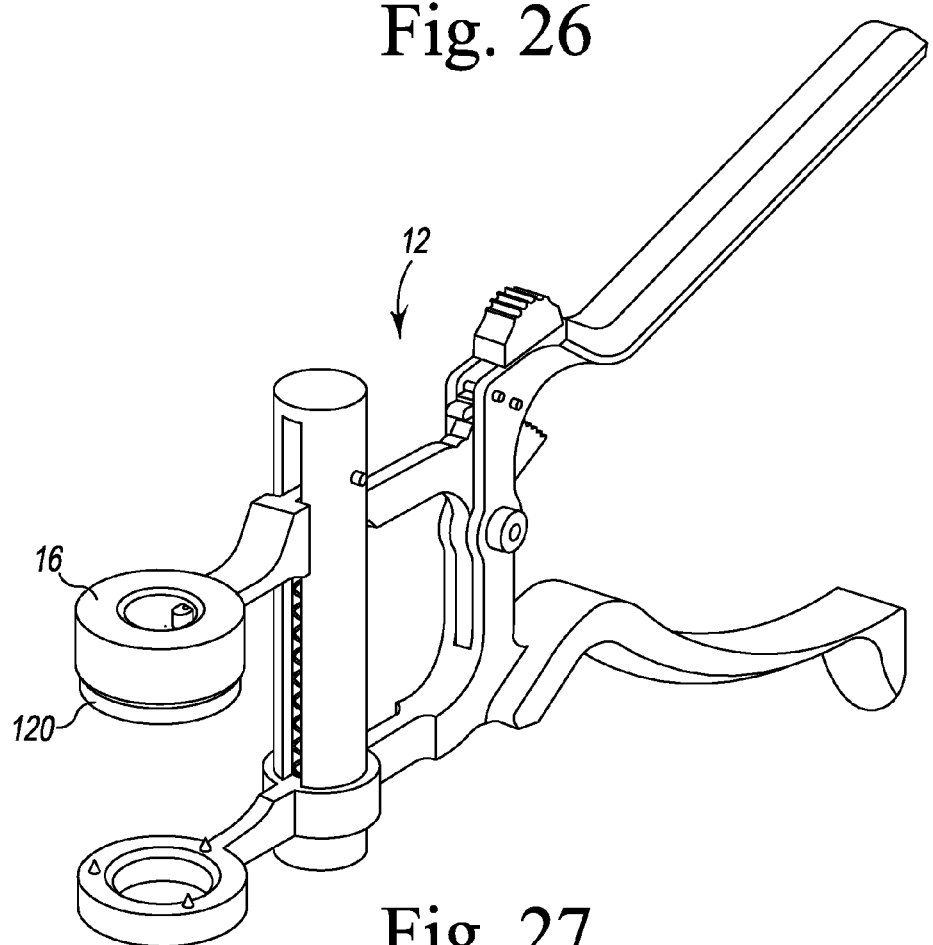
Figure 28:
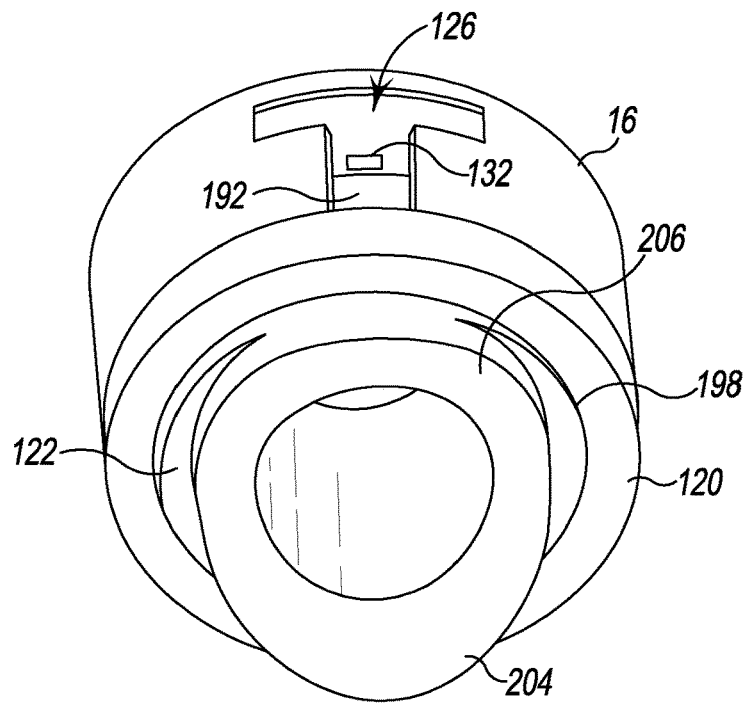
Figure 29:
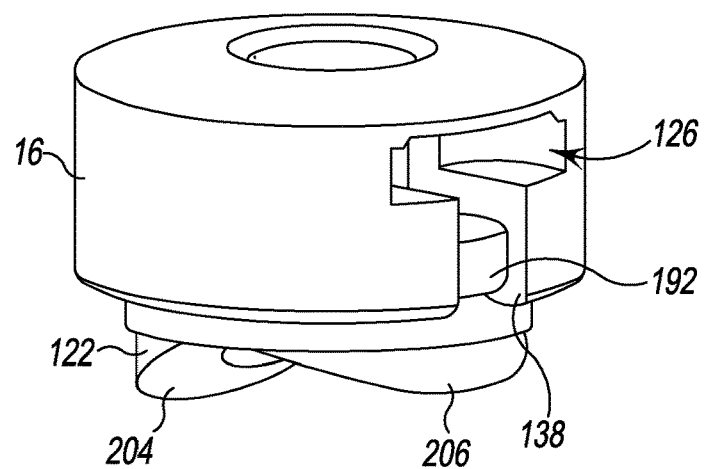
Figure 30:
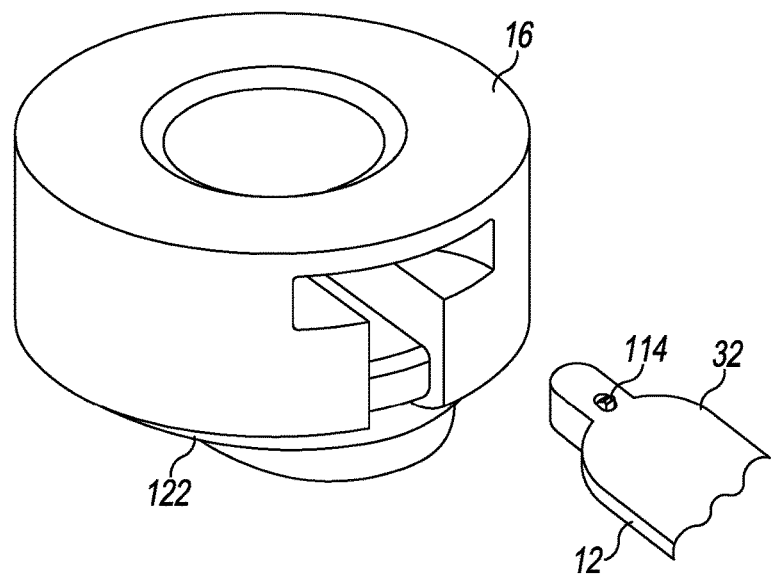
Figure 31:
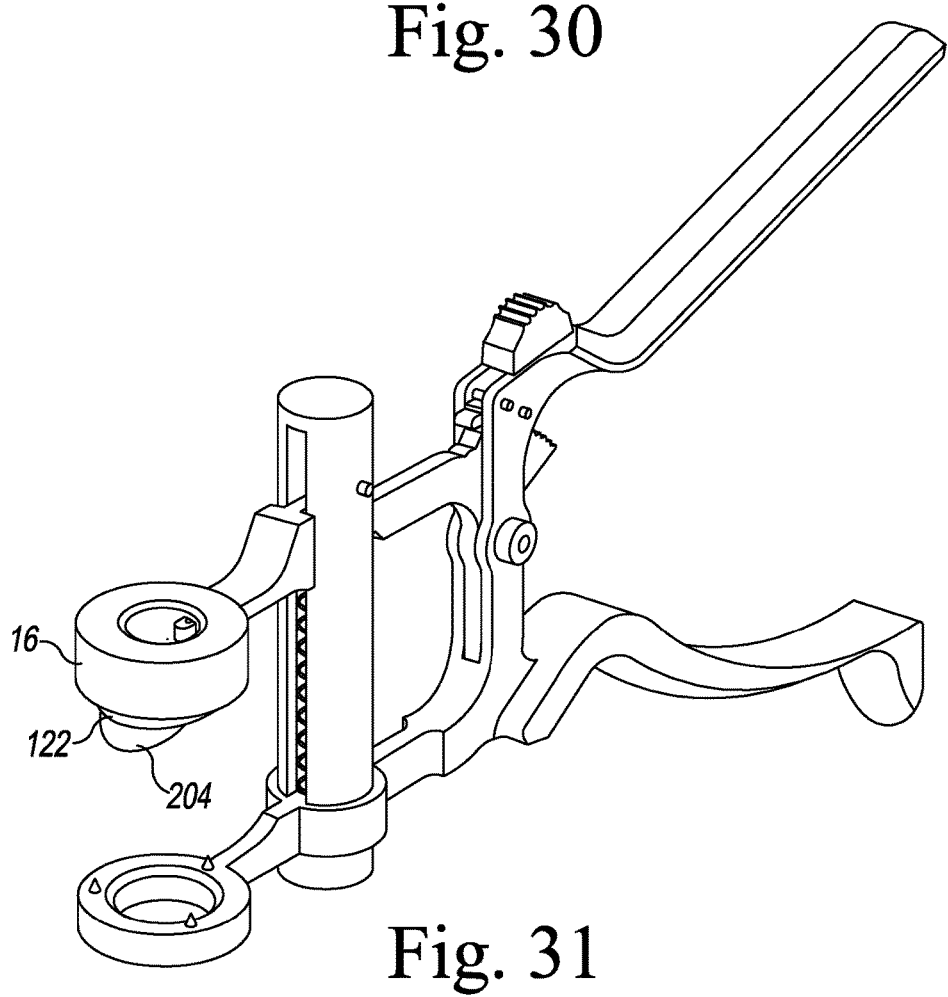

Referring now to FIGS. 19-21, there is shown a surgical procedure in which the various instruments described herein in regard to FIGS. 1-17 are used to surgically prepare the patient's patella 300 for implantation of one of the prosthetic patella components 302 of FIG. 18. The surgical procedure begins with preoperative planning in which, amongst other things, a CT scan or other type of preoperative image may be obtained to plan the placement location and orientation of the patella component 302. With the preoperative planning complete, the patient's soft tissue is dissected and retracted in order to allow access to the knee. Full exposure of the patient's joint is typically achieved so as to expose, in addition to the patella 300, the patient's femur 350 and tibia 352.

In addition to implantation of one of the patella components 302, the surgical procedure also replaces the patient's natural distal femur 350 with a prosthetic femoral component 304 and the patient's natural proximal tibia 352 with a tibial tray 356 and tibial bearing 358. However, the surgical implantation of the femoral component 304, the tibial tray 356, and tibial bearing 358 is not described in detail herein. Moreover, although the patella 300 is shown in its anatomical position relative to the femur 350 and the tibia 352 in FIG. 19, the patella 300 is shown in isolation from its anatomical position in the remaining figures for clarity of description.

To prepare the posterior surface of the patient's patella, the surgeon may then resect the patient's natural patella 300. Specifically, the surgeon may use a resection guide (not shown) and a bone saw (also not shown) to produce a generally planar surgically-resected patellar surface 370 onto which the patella component 302 will be subsequently implanted. Although numerous different instruments and methods may be used to resect the patient's natural patella 300, illustrative instruments and methods for doing so are described in commonly-owned, co-pending U.S. Pat. No. 8,986,306, which is entitled "Patella Orthopaedic Surgical Method."

The surgeon may then select an appropriately-sized patella drill guide and trial instrument 14. Once the patella drill guide and trial instrument 14 of the proper size has been selected, the surgeon may secure the patella drill guide and trial instrument 14 to the surgically-resected patellar surface 370. To do so, the surgeon positions the patella drill guide and trial instrument 14 in a desired location and orientation for the final implant (i.e., the patella component 302) by aligning the alignment bore 90 of the selected patella drill guide and trial instrument 14 with a drilled alignment hole (not shown). So positioned, the spikes 70 of the patella drill guide and trial instrument 14 face downwardly toward the surgically-resected patellar surface 370, and the patella drill guide and trial instrument 14 may be pressed into the surgically-resected patellar surface 370.

It should be appreciated that the surgeon may press the patella drill guide and trial instrument 14 into the bone tissue of the surgically-resected patellar surface 370 by hand with the application of finger pressure alone. However, in certain cases, it may be necessary to utilize additional force in order to fully seat the patella drill guide and trial instrument 14 in the surgically-resected patellar surface 370. In such cases, the surgeon may install the removable clamp 12 to the patella drill guide and trial instrument 14 and use the clamp 12 to apply a clamping force which urges the instrument's spikes 60 into the bone tissue of the surgically-resected patellar surface 370 so as to fully seat the patella drill guide and trial instrument 14.

Once the patella drill guide and trial instrument 14 has been installed on the surgically-resected patellar surface 370, the surgeon may then perform a trial of the patellofemoral joint to assess size and positioning. To do so, the surgeon first installs the alignment handle 230 to the patella drill guide and trial instrument 14. Use of the alignment handle 230 allows the surgeon to assess the rotational alignment of the patella drill guide and trial instrument 14 as it articulates in the trochlear groove of the femoral component 304 during trialing of the patellofemoral joint. To secure the alignment handle 230 to the patella drill guide and trial instrument 14, the surgeon inserts the handle's connector 234 into the connecting slot 102 of the patella drill guide and trial instrument 14. In doing so, the handle's plunger 240 is captured in the locking recess 112 of the connecting slot 102 of the patella drill guide and trial instrument 14 to firmly secure the alignment handle 140 to the patella drill guide and trial instrument 14.

Once the alignment handle 230 is installed, the surgeon may then position the patella drill guide and trial instrument 14 such that its posterior trial bearing surface 62 is positioned to articulate within the trochlear groove 310 of the femoral condyle surfaces 306, 308 of the femoral component 304, as shown in FIG. 19. The surgeon may then manipulate the patient's leg so as to perform a trial articulation of the patellofemoral joint. In doing so, the surgeon may use the alignment handle 230 as a visual indicator of the rotational alignment of the patella drill guide and trial instrument 14 as it articulates in the trochlear groove 310 of the femoral component 304. Specifically, as shown in FIG. 19, if the medial edge of the patella drill guide and trial instrument 14 (i.e., the edge into which the connecting slot 102 is formed) is properly aligned, the alignment handle 230 extends outwardly in a direction generally perpendicular to the long axis of the femur and tibia. That is, it extends outwardly generally in the medial/lateral direction.

Based on the above, the surgeon may assess the rotational position and alignment of the patella drill guide and trial instrument 14 throughout a trial articulation of the patellofemoral joint by monitoring the position of the alignment handle 230. If at any time during the trialing procedure the alignment handle 230 does not maintain the desired angle relative to the long axis of the femur and tibia (i.e., it does not extend generally in the medial/lateral direction), the surgeon may perform a corrective procedure on the positioning of the patella drill guide and trial instrument 14 to improve the rotational positioning thereof.

Once the surgeon has completed the trial articulation of the patellofemoral joint and made any necessary adjustments to the position of the patella drill guide and trial instrument 14, the surgeon may then drill a number of anchor holes 380 in the surgically-resected patellar surface 370. The anchor holes 380 are sized and positioned to receive the anchor pegs of the selected patella component 302. To do so, the surgeon first secures the removable clamp 12 to the patella drill guide and trial instrument 14 by advancing the clamp's connector 32 into the connecting slot 102 of the patella drill guide and trial instrument 14. In doing so, the handle's plunger 114 is captured in the locking recess 112 of the connecting slot 102 of the patella drill guide and trial instrument 14 to firmly secure the patella clamp 12 to the patella drill guide and trial instrument 14.

The surgeon then squeezes the clamp's handles 26, 30 toward one another, thereby moving the patella drill guide and trial instrument 14 and the retaining socket 28 toward one another so as to clamp the patella 300 therebetween. With the patella 300 secured by the clamp 12, the surgeon may now drill the anchor holes 380. To do so, the surgeon may advance the rotating tip of the surgical drill's bit 84 into the opening formed in the posterior trial bearing surface 62 of one of the drill guide holes 76 and through the patella drill guide and trial instrument 14 so that it exits the guide hole 76 through the instrument's anterior surface 68 and enters the bone tissue of the surgically-resected patellar surface 370. The surgeon may then drill the remaining anchor holes 180 in a similar manner.

As noted above, the size and position of each of the drill guide holes 76 coincides with the size and position of the anchor pegs of the patella component 302. As such, once the surgeon has advanced the drill's surgical bit 84 through each of the guide holes 76, the surgically-resected patellar surface 370 is prepared for implantation of one of the patella components 302.

Referring now to FIG. 21, once the anchor holes 380 have been drilled in the surgically-resected patellar surface 370, the surgeon may select an appropriately sized patella component 314 or an appropriately sized patella component 316 for implantation. If the surgeon selects a dome-shaped patella component 314, the surgeon may apply bone cement to the anterior surface of the patella component 314. The patella component 314 is then positioned over the surgically-resected patellar surface 370 such that the component's anchor pegs are aligned with their respective anchor holes 380. Thereafter, the patella component 314 may be advanced such that the anchor pegs are received into the anchor holes 380 and the anterior surface is positioned in contact with the surgically-resected patellar surface 370.

The surgeon may then select the compressible base 18 corresponding to the selected component 302. If the component 314 is selected, the surgeon selects the dome patella base 120 and attaches the base 120 to the socket body 124. To do so, the surgeon aligns the orientation tab 150 of the base 120 with the orientation groove 146 of the socket body 124. The surgeon may then advance the base 120 into the body 124 such that the plug 162 is advanced into the receptacle 144 defined in the socket body 124. The plug 162 may deform slightly as it enters the receptacle before the outer flange 166 engages the annular flange 138 of the socket body 124, thereby securing the dome patella base 120 to the socket body 124.

The removable clamp 12 may then be secured to the compression socket 16 and base 120 by inserting the clamp's connector 32 into the socket's connecting slot 126. The compression socket 16 may then be used to assert clamping pressure on the patella component 302 as it is cemented in place on the patient's resected patella 300. That is, the compression socket 16 and clamp 12 may be used to maintain clamping pressure on the patella component 302 as the bone cement polymerizes. To do so, the base 120 of the compression socket 16 is positioned over the posterior bearing surface 320 of the patella component 314. The surgeon then squeezes the clamp's handles 26, 30 toward one another, thereby moving the compression socket 16 and the retaining socket 28 toward one another. During such movement, the base 120 of the compression socket 16 is advanced into contact with the posterior bearing surface 320 of the patella component 314. The patella component 314 is seated within and stabilized by a concave surface 172 of the compressible base 120 such that the patella component 314 is clamped firmly to the resected patella 300 until polymerization is complete and the patella component 314 is secured thereto. The surgeon may slide the patella clamp's button 48 forward to lock the clamp 12 in its current position during the polymerization process.

As described above, the button 48 of the clamp 12 engages a locking pawl 50 such that the locking pawl 50 is disengaged from the ratchet teeth 46 by sliding the button 48 in the opposite direction. When the locking pawl 50 is disengaged from the ratchet teeth 46, the levers 20, 22 of the patella clamp 12 are free to move relative to one another and release the instrument 14 from the patella 300. In the event of jamming, the surgeon may pull on the flange 52 in the direction indicated by arrow 54 to manually release the locking pawl 50 and free the levers 20, 22 of the patella clamp 12 to move relative to one another.

If the anatomic patella prosthetic component 316 is selected, the surgeon may select the anatomic patella base 122 and attach the base 122 to the socket body 124. To do so, the surgeon aligns the orientation tab 150 of the base 122 with the orientation groove 146 of the socket body 124. The surgeon may then advance the base 122 into the body 124 such that the plug 190 is advanced into the receptacle 144 defined in the socket body 124. The plug 190 may deform slightly as it enters the receptacle before the outer flange 192 engages the annular flange 138 of the socket body 124, thereby securing the anatomic patella base 122 to the socket body 124.

The removable clamp 12 may then be secured to the compression socket 16 and base 120 by inserting the clamp's connector 32 into the socket's connecting slot 126. The compression socket 16 may then be used to assert clamping pressure on the patella component 316 as it is cemented in place on the patient's resected patella 300. That is, the compression socket 16 and clamp 12 may be used to maintain clamping pressure on the patella component 302 as the bone cement polymerizes. To do so, the base 120 of the compression socket 16 is positioned over the posterior bearing surface 320 of the patella component 314. In the illustrative embodiment, the lateral wedge 204 is aligned with the concave section 334 of the lateral articular surface 322 of the component 316, while the medial wedge 206 is aligned with the convex section 336 of the medial articular surface 324 of the component 316.

The surgeon then squeezes the clamp's handles 26, 30 toward one another, thereby moving the compression socket 16 and the retaining socket 28 toward one another. During such movement, the base 122 of the compression socket 16 is advanced into contact with the posterior bearing surface 320 of the patella component 316 such that the lateral wedge 204 is is received in the concave section 334 of the lateral articular surface 322 of the component 316, while with the convex section 336 of the medial articular surface 324 of the component 316 is received in the medial wedge 206 of the base 122. In that way, the patella component 316 is stabilized by the wedges 204, 206 of the compressible base 122 such that the patella component 316 is clamped firmly to the resected patella 300 until polymerization is complete and the patella component 314 is secured thereto. The surgeon may slide the patella clamp's button 48 forward to lock the clamp 12 in its current position during the polymerization process.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument system, comprising:
   a first patella component configured to selectively engage a surgically prepared end of a patient's patella, the first patella component including a convex, curved posterior surface,
   a second patella component configured to selectively engage a surgically prepared end of a patient's patella, the second patella component includes a body, a medial peak extending posteriorly from the body, and a lateral peak extending posteriorly from the body, the medial peak and the lateral peak cooperating to define a posterior surface of the second patella component,
   a clamp comprising a first lever pivotally coupled to a second lever, wherein (i) a proximal end of the first lever includes an upper handle and a distal end of the first lever includes a retaining socket secured thereto, and (ii) a proximal end of the second lever includes a lower handle and a distal end of the second lever includes a connector,
   a patella drill guide and trial instrument having a connector configured to be selectively secured to the connector of the clamp, the patella drill guide and trial instrument comprising (i) a posterior trial bearing surface configured to articulate with a condylar surface of a prosthetic femoral component, (ii) an anterior surface opposite the posterior trial bearing surface and having a number of spikes extending outwardly therefrom, and (iii) a number of drill guide holes extending from the posterior trial bearing surface to the anterior surface,
   a compression socket having a connector configured to be selectively secured to the connector of the clamp in place of the patella drill guide and trial instrument, the compression socket having a receptacle defined in an anterior surface, and
   a number of compressible bases configured to be selectively received in the receptacle of the compression socket, each compressible base including an anterior surface having a different shape from every other compressible base,
   wherein the number of compressible bases includes (i) a first compressible base, the anterior surface of the first compressible base having a circular rim and a concavely curved surface extending inwardly from the circular rim that is shaped to engage the posterior surface of the first patella component, and (ii) a second compressible base that includes a body, a medial wedge extending anteriorly from the body, and a lateral wedge extending anteriorly from the body, the medial wedge and the lateral wedge cooperating to define the anterior surface of the second compressible base, the anterior surface of the second compressible base being shaped to engage the posterior surface of the second patella component.

2. The orthopaedic surgical instrument system of claim 1, wherein the circular rim has a medial width and a lateral width that is greater than the medial width.

3. The orthopaedic surgical instrument system of claim 1, wherein the first compressible base has a medial thickness and a lateral thickness that is greater than the medial thickness.

4. The orthopaedic surgical instrument system of claim 3, wherein:
the circular rim includes a lateral section that defines a first imaginary plane and a medial section that defines a second imaginary plane, and
a non-zero angle is defined between the first imaginary plane and the second imaginary plane.

5. The orthopaedic surgical instrument system of claim 1, wherein the medial wedge is connected to the lateral wedge to define an oblong shape.

6. The orthopaedic surgical instrument system of claim 1, wherein the medial wedge includes a concavely curved anterior surface that defines a portion of the anterior surface of the second compressible base.

7. The orthopaedic surgical instrument system of claim 6, wherein the lateral wedge includes a convexly curved anterior surface that defines a second portion of the anterior surface of the second compressible base.

8. The orthopaedic surgical instrument system of claim 1, wherein:
the medial wedge has a maximum thickness, and
the lateral wedge has a maximum thickness greater than the maximum thickness of the medial wedge.

9. The orthopaedic surgical instrument system of claim 1, wherein the compression socket includes an annular flange configured to selectively engage and retain each compressible base in the receptacle.

10. The orthopaedic surgical instrument system of claim 1, wherein each compressible base includes a posteriorly-extending tab to orient the compressible base in the receptacle of the compression socket.

11. The orthopaedic surgical instrument system of claim 1, wherein:
the compression socket comprises a ring having the receptacle and a connecting slot formed therein, and
the connector of the clamp includes a connecting tongue configured to be received into the connecting slot of the compression socket so as to secure the compression socket to the clamp.

* * * * *